US011268152B2

(12) United States Patent
Chen et al.

(10) Patent No.: US 11,268,152 B2
(45) Date of Patent: Mar. 8, 2022

(54) MARKERS OF BREAST CANCER AND METHODS FOR THE USE THEREOF

(71) Applicant: CITY OF HOPE, Duarte, CA (US)

(72) Inventors: Shiuan Chen, Arcadia, CA (US); Hei Jason Chan, Alhambra, CA (US)

(73) Assignee: CITY OF HOPE, Duarte, CA (US)

( * ) Notice: Subject to any disclaimer, the term of this patent is extended or adjusted under 35 U.S.C. 154(b) by 0 days.

(21) Appl. No.: 15/543,921

(22) PCT Filed: Jan. 19, 2016

(86) PCT No.: PCT/US2016/013970
§ 371 (c)(1),
(2) Date: Jul. 14, 2017

(87) PCT Pub. No.: WO2016/115572
PCT Pub. Date: Jul. 21, 2016

(65) Prior Publication Data
US 2018/0264109 A1 Sep. 20, 2018

Related U.S. Application Data

(60) Provisional application No. 62/104,595, filed on Jan. 16, 2015.

(51) Int. Cl.
C12Q 1/6886 (2018.01)
C12Q 1/686 (2018.01)

(52) U.S. Cl.
CPC ........... C12Q 1/6886 (2013.01); C12Q 1/686 (2013.01); C12Q 2600/106 (2013.01); C12Q 2600/112 (2013.01); C12Q 2600/158 (2013.01)

(58) Field of Classification Search
None
See application file for complete search history.

(56) References Cited

U.S. PATENT DOCUMENTS

| | | | | |
|---|---|---|---|---|
| 9,663,831 B2* | 5/2017 | Apte | .................. | C12Q 1/6888 |
| 2011/0217297 A1* | 9/2011 | Kao | ................ | G01N 33/57415 424/133.1 |
| 2013/0071856 A1 | 3/2013 | Liao et al. | | |
| 2013/0190386 A1* | 7/2013 | Croce | .................. | C12Q 1/6886 514/44 A |
| 2014/0357518 A1* | 12/2014 | Chapman | ............. | C12Q 1/6886 506/9 |

OTHER PUBLICATIONS

NCBI Database GEO Profile for GI: 383286745; available via URL: <ncbi.nlm.nih.gov/geoprofiles/?term=GI%3A383286745>, printed on Feb. 26, 2019.*
Affymetrix NefAttx. Details for HG-U133 Plus 2: 202833_s_at; available at URL: <affymetrix.com/analysis/netaffx/fullrecord.affx?pk=HG-U133_PLUS_2:202833_S_AT>, printed on Feb. 26, 2019.*
Affymetrix NetAffx Details for HG-U133 Plus 2:202627_s_at (available via URL: <affymetrix.com/analysis/netaffx/fullrecord.affx?pk=HG-U133_PLUS_2:202627_S_AT>, printed on Feb. 26, 2019.*
Gone et al Cancer Research. Dec. 2012. Supp. 3:72.24.*
Farshchian et al Am J Pathology. Sep. 2011. 179: 1110-1119.*
Arora et al. J Proteomics Bioinform. May 2013. 6(5): 099-098.*
Wikipedia—Alpha-1 antitrypsin (available via URL: <wikipedia.org/wiki/Alpha-1_antitrypsin>, printed on Feb. 27, 2019, pp. 6-14.*
BreastCancer.org. "Molecular Subtypes of Breast Cancer," available via URL: < breastcancer.org/symptoms/types/molecular-subtypes>, printed on Oct. 13, 2021 (Year: 2021).*
Dawood, S. et al. (Jan. 1, 2010, e-published Nov. 23, 2009). "Prognosis of women with metastatic breast cancer by HER2 status and trastuzumab treatment: an institutional-based review," J Clin Oncol 28(1):92-98.
Desmet, C.J. et al. (Mar. 26, 2013, e-published Mar. 12, 2013). "Identification of a pharmacologically tractable Fra-1/ADORA2B axis promoting breast cancer metastasis," PNAS USA 110(13):5139-5144.
Desmedt, C. et al. (Jun. 1, 2007). "Strong time dependence of the 76-gene prognostic signature for node-negative breast cancer patients in the TRANSBIG multicenter independent validation series," Clin Cancer Res 13(11):3207-3214.
Farshchian. M. et al. (Sep. 2011, e-published Jul. 1, 2011). "Serpin peptidase inhibitor clade A member 1 (SerpinA1) is a novel biomarker for progression of cutaneous squamous cell carcinoma," Am J Pathol 179(3):1110-1119.
International Search Report dated May 13, 2016, for PCT Application No. PCT/US2016/013970, filed Jan. 19, 2016, 5 pages.
Jerjees, D.A. et al. (Jun. 2014, e-published Apr. 18, 2014). "Prognostic and biological significance of proliferation and HER2 expression in the luminal class of breast cancer," Breast Cancer Res Treat 145(2):317-330.
Masri, S. et al. (Jun. 15, 2008). "Genome-wide analysis of aromatase inhibitor-resistant, tamoxifen-resistant, and long-term estrogen-deprived cells reveals a role for estrogen receptor," Cancer Res 68(12):4910-4918.
Sotiriou, C. et al. (Sep. 2, 2003, e-published Augugst 13, 2003). "Breast cancer classification and prognosis based on gene expression profiles from a population-based study," PNAS USA 100(18):10393-10398.
Valeria de Sa, S. et al. (Sep. 15, 2007, e-published Sep. 12, 2007). "Serpin peptidase inhibitor clade A member 1 as a potential marker for malignancy in insulinomas," Clin Cancer Res 13(18 Pt 1):5322-5330.

(Continued)

Primary Examiner — Carla J Myers
(74) Attorney, Agent, or Firm — Mintz, Levin, Cohn, Ferris, Glovsky and Popeo, P.C.

(57) ABSTRACT

In accordance with the present invention, the single gene SERPINA1 has been identified as a significant predictor of survival in ER+ and ER+/HER2+ breast cancer patients. For example, patients with ER+/FIER2+ breast cancer generally have a worse outcome compared to ER+/FIER2− and ER−/FIER2+ patients. Currently there is no known predictive marker for the treatment C outcome of ER+ and ER+/FIER2+ breast cancers, thus the ability of SERPINA1 to predict the survival of this intrinsic subtype of breast cancer patients is valuable.

4 Claims, 12 Drawing Sheets
Specification includes a Sequence Listing.

(56) References Cited

OTHER PUBLICATIONS

Vierlinger, K. et al. (Apr. 6, 2011). "Identification of SERPINA1 as single marker for papillary thyroid carcinoma through microarray meta analysis and quantification of its discriminatory power in independent validation," *BMC Med Genomics* 4:30.
Written Opinion dated May 13, 2016, for PCT Application No. PCT/US2016/013970, filed Jan. 19, 2016, 5 pages.
Zhao, W. et al. (Jun. 2013, e-published Apr. 23, 2013). "Identification of α1-antitrypsin as a potential prognostic biomarker for advanced nonsmall cell lung cancer treated with epidermal growth factor receptor tyrosine kinase inhibitors by proteomic analysis," *J Int Med Res* 41(3):573-583.

\* cited by examiner

FIG. 3A (1)
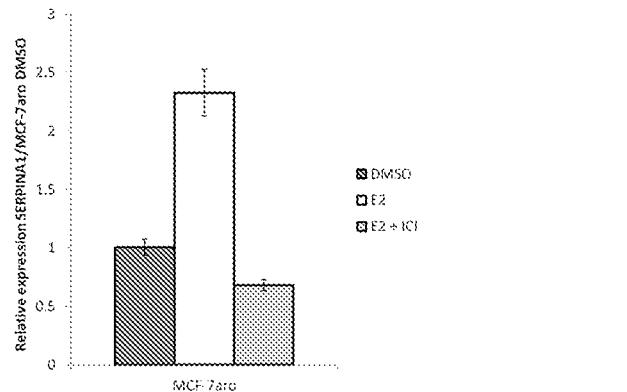
FIG. 3A (2)
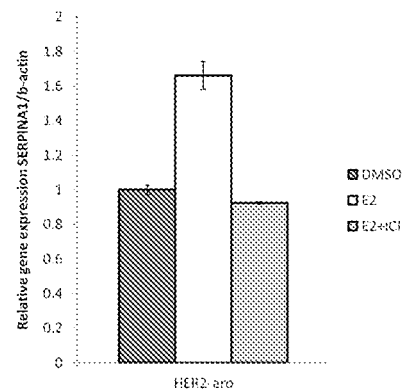
FIG. 3A (3)
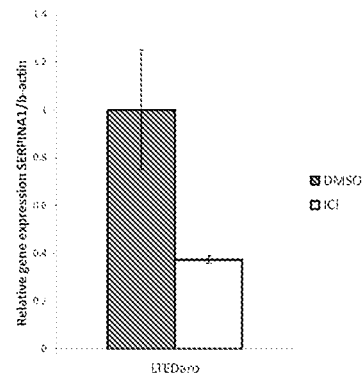

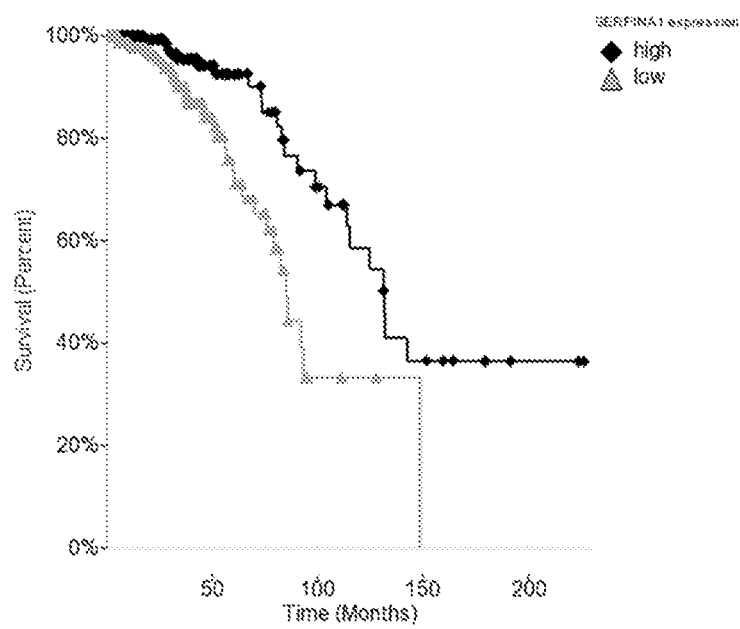
ER+ patients (n=570, p=0.0002)
FIG. 4A (1)
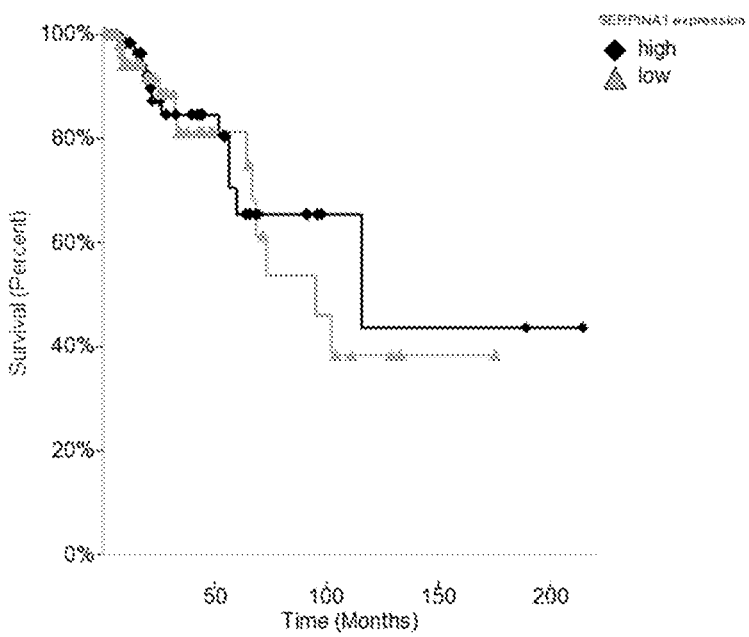
ER- patients (n=172, p=0.66)
FIG. 4A (2)

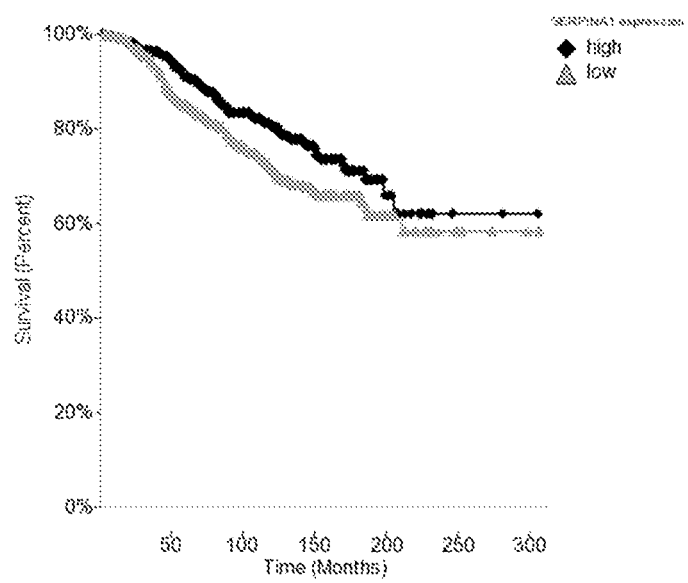
ER+ patients (n=986, p=0.010)
FIG. 4B (1)
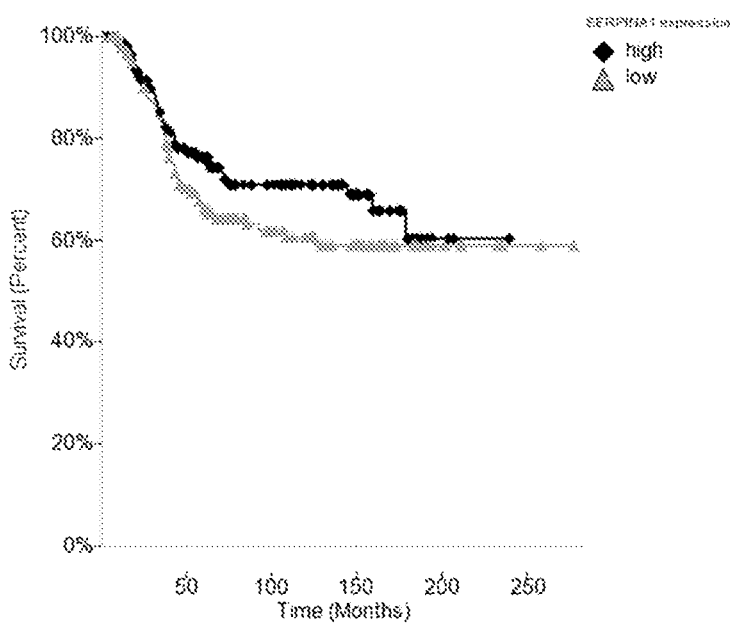
ER- patients (n=298, p=0.20)
FIG. 4B (2)

TFF1 gene, ER+ patients  PGR gene, ER+ patients  GREB1 gene, ER+
patients
(n=494, p=0.08)         (n=494, p=0.19)          (n=494, p=0.95)

TFF1 gene, ER+/HER2+           PGR gene, ER+/HER2+         GREB1 gene,
ER+/HER2+ patients (n=82, p=0.38)   patients (n=82, p=0.16)    patients
(n=82, p=0.62)

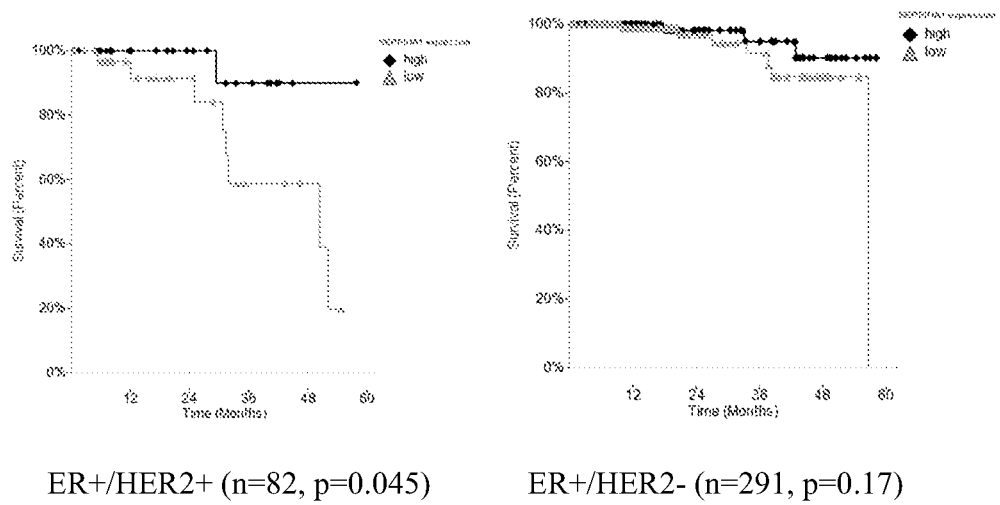
ER+/HER2+ (n=82, p=0.045)    ER+/HER2- (n=291, p=0.17)
FIG. 5A
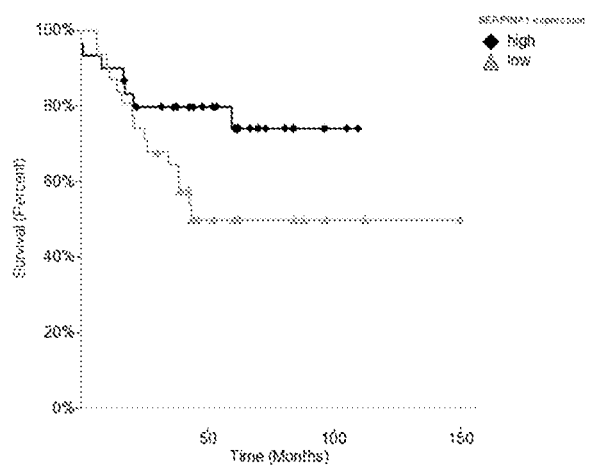
ER+/HER2+ (n=61, p=0.075)
FIG. 5B (1)

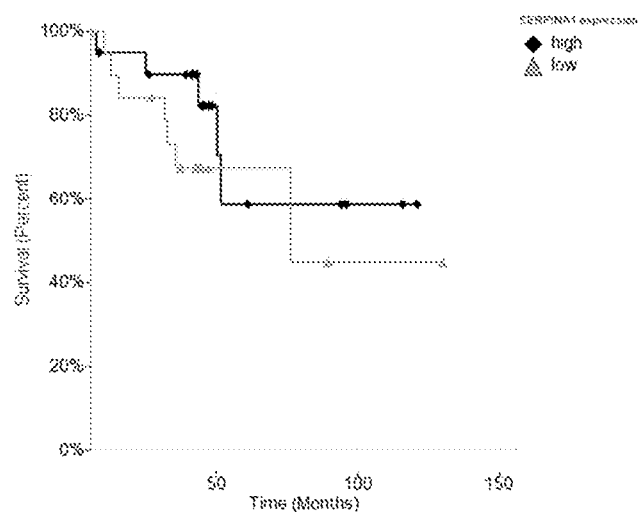
ER+/HER2- (n=40, p=0.33)
FIG. 5B (2)

MARKERS OF BREAST CANCER AND METHODS FOR THE USE THEREOF

CROSS-REFERENCES TO RELATED APPLICATIONS

This application is the national stage filing under USC 371 of international application PCT/US2016/013970, filed Jan. 19, 2016, which claims the benefit U.S. Provisional Appl. No. 62/104,595, filed Jan. 16, 2015, the contents of which are incorporated herein by reference in their entireties and for all purposes.

REFERENCE TO A "SEQUENCE LISTING," A TABLE, OR A COMPUTER PROGRAM LISTING APPENDIX SUBMITTED AS AN ASCII FILE

The Sequence Listing written in file 48440-543001US_ST25.TXT, created Jan. 19, 2015, 6,140 bytes, machine format IBM-PC, MS-Windows operating system, is hereby incorporated by reference.

FIELD OF THE INVENTION

The present invention relates to novel markers of human breast cancer, and methods for the use thereof. In certain aspects, the invention relates to complexes, kits and compositions comprising the above-described markers. In certain aspects, the invention relates to methods of treating breast cancer.

BACKGROUND OF THE INVENTION

The information provided herein and references cited are provided solely to assist the understanding of the reader, and does not constitute an admission that any of the references or information is prior art to the present invention.

The estrogen receptor alpha (ER) is a crucial transcription factor that is required for cell proliferation in the majority of breast cancer cases, accounting for about 70% of all breast cancers. A major treatment of ER+ breast cancer is endocrine therapy using anti-estrogens like tamoxifen or aromatase inhibitors (AIs). However, a significant number of ER+ patients are not responsive to such treatment (i.e., de novo resistance) and some patients develop resistance during endocrine therapy (i.e., acquired resistance).

Previous studies have shown that the ER is required for growth in both endocrine (therapy)-responsive and endocrine-resistant breast cancer cells, but only endocrine-responsive cells require estrogen for the proliferation (1). The global genomic binding profile of ER has been well documented in hormone-responsive breast cancer cells but not in hormone-resistant cells (2). Genomic profiling and data mining using large patient cohorts can broaden the current view of biomarkers involved in ER-mediated regulatory mechanisms and clinical relevance.

About 10% of all breast cancer patients are ER+/HER2+, and these patients have a worse outcome compared to ER+/HER2− patients. Currently there is a lack of effective prognosis biomarkers for the prediction of outcome in ER+/HER2+ patients, and the treatment options are limited.

SUMMARY OF THE INVENTION

In accordance with one aspect of the present invention, a novel biomarker, SERPINA1, has been identified for the prediction of the outcome in ER+ and ER+/HER2+ breast cancer patients. Patients expressing high levels of this gene have better outcome.

As a result of extensive ER ChIP-seq analysis, the inventors have identified a gene, SERPINA1, that has a clear ER binding site in its promoter region and higher expression level in LTEDaro DMSO (i.e., in the absence of E2). The levels of SERPINA1 mRNA have been found to be significantly higher in LTEDaro DMSO than in E2-treated MCF-7aro E2 (1). Based on survival analysis results using the publicly available large panel of The Cancer Genome Atlas (TCGA) 779 breast cancer patient cohort (6) with clinicopathological information, it has been determined that the high expression of SERPINA1 in endocrine-resistant cells requires HER2 and has significant association with better survival outcome for ER+ and ER+/HER2+ breast cancer; thus SERPINA1 can be used as a molecular predictor of drug response in breast cancers.

SERPINA1, also known as α1-AntiTrypsin (AAT), is a protease inhibitor that can act on a variety of targets such as serine proteases. It has been demonstrated that SERPINA1 expression can be stimulated by E2 in MCF-7 cells, and high expression of this protein inhibits colony formation [7]. SERPINA1 has been proposed as a biomarker for various diseases such as Cutaneous Squamous Cell Carcinoma [8], Hepatitis B [9], insulinomas [10], NSCLC [11], papillary thyroid carcinoma [12] lung cancer [13] and breast carcinoma [14-16]. The results presented herein support the proposition that the single gene SERPINA1 is a significant predictor of survival in ER+ and ER+/HER2+ breast cancer patients. Patients with ER+/HER2+ breast cancer generally have a worse outcome compared to ER+/HER2− patients [17,18]. Currently there is no known predictive marker for the treatment outcome of ER+/HER2+ breast cancers (19), thus the ability of SERPINA1 to predict the survival of this intrinsic subtype of breast cancer patients is valuable.

Thus, in order to advance the present invention, an aromatase-overexpressing MCF-7 cell line, i.e., MCF-7aro (3), has been generated and the resulting MCF-7aro cells used as a model for endocrine-responsive breast cancer. In addition, Long Term Estrogen Deprived (LTEDaro) cells are used as a model for endocrine-resistant breast cancer (4).

In the endocrine-responsive breast cancer cells, 17β-estradiol (E2) acts as a ligand and binds to ER, activating the ER and causing its translocation from the cytosol to the nucleus. The E2-bound ER then binds to the chromatin to regulate the expression of target genes.

In the endocrine-resistant cells, the ER can be activated by other mechanisms such as phosphorylation, so even in the absence of E2, the ER is able to bind to chromatin and activate target genes. The ligand-independent activation of ER is thought to play a key role in endocrine-resistant breast cancer because the ER degrader, fulvestrant (ICI 182,780), is able to suppress the expression of ER-regulated genes (5). In accordance with the present invention, ER binding sites and target genes have been identified which assist in understanding the role of ER in endocrine resistant cancer.

Therefore, to better understand the physiological action of ER-target genes, chromatin immunoprecipitation with deep sequencing (ChIP-seq) genome-wide profiling was used as a tool to identify differences in ER binding between endocrine-responsive and endocrine-resistant cell lines. In previous studies, Affymetrix GENECHIP® genome-wide microarray gene expression analysis has been performed to detect differentially expressed estrogen-regulated genes (1), but these target genes include direct and also indirect ER targets. The combination of ChIP-seq with microarray gene expression analyses allows identification of the direct ER target genes. Without wishing to be bound by any theory, it is believed that the identification of such genes would allow for the identification of a gene that acts as a biomarker for endocrine-resistant breast cancer. Such a biomarker would be valuable for the prediction of patient response to endocrine therapy and could facilitate the selection of the most effective treatment options for patients.

BRIEF DESCRIPTION OF THE DRAWINGS

FIG. 1A demonstrates the distribution of ER binding sites relative to the closest TSS. It is observed that MCF-7aro DMSO binding sites are almost evenly distributed and MCF-7aro E2 binding sites are more abundant close to the TSS. LTEDaro DMSO binding sites are abundant close to the TSS with a similar trend as the MCF-7aro E2. FIG. 1B provides a correlation between the number of binding sites and binding intensities of LTEDaro DMSO and MCF-7aro E2. FIG. 1C provides a comparison of LTEDaro DMSO and MCF-7aro E2, and shows that a majority of ER binding sites occur at the same location, although the intensities may be different.

FIG. 2A presents a summary of bioinformatics analysis of ILLUMINA® ChIP-seq and Affymetrix GENECHIP® gene expression microarray data, leading to the discovery of SERPINA1 and its potential regulation by ER and HER2. FIG. 2B illustrates the fact that SERPINA1 has an ER binding site proximal to the TSS with higher level of ER binding in the LTEDaro DMSO cells compared to MCF-7aro E2 cells. In contrast, other well-known ER target genes have higher level of ER binding in the MCF-7aro E2 cells instead. FIG. 2C provides ChIP PCR validation of ER binding site proximal to the TSS of SERPINA1 confirms the ER binding in LTEDaro, as detected by ChIP-seq.

FIGS. 3A-3B collectively demonstrate that E2 and HER2 regulate the expression of SERPINA1 through the ER. FIG. 3A presents gene expression analysis of SERPINA1 by qPCR, and shows that SERPINA1 expression in MCF-7aro E2, HER2-aro E2, and LTEDaro DMSO can be suppressed by ICI treatment. FIG. 3B presents a comparison of SERPINA1 expression in control-siRNA treated cells, and demonstrates that HER2-aro and LTEDaro cells have a higher expression compared to MCF-7aro. siRNA knockdown of HER2 shows that SERPINA1 is downregulated by about 40% when HER2 levels are reduced.

FIGS. 4A-4D collectively support the position that SERPINA1 expression level is a predictive marker for patient survival in ER+ but not ER− patients. FIG. 4A presents a survival analysis in the TCGA cohort of ER+ and ER− patients, and shows that SERPINA1 has a significant predictive value only in the ER+ patients but not the ER− patients. FIG. 4B presents validation with ER+ and ER− patients in the Curtis cohort, confirming that SERPINA1 has a significant predictive value in ER+ but not ER− patients. FIG. 4C summarizes the overall survival in TCGA ER+ patients with high and low expression of 3 common ER target genes: pS2, PGR, GREB1 by Kaplan Meier survival analysis. FIG. 4D summarizes the overall survival in TCGA ER+/HER2+ patients with high and low expression of 3 common ER target genes: pS2, PGR, GREB1 by Kaplan Meier survival analysis.

FIGS. 5A-5B collectively present a survival analysis of SERPINA1 in TCGA and Bild patient cohorts with ER+/HER2+ status. FIG. 5A demonstrates that the SERPINA1 gene has a significant predictive value in the ER+/HER2+ but not the ER+/HER2− patients from the TCGA cohort. FIG. 5B presents validation with ER+/HER2+ and ER+/HER2-patients in the Bild cohort. Disease-free survival analysis of ER+/HER2+ patients in the Bild patient cohort shows that patients with high expression of SERPINA1 has a better outcome.

DETAILED DESCRIPTION OF THE INVENTION

ER is a key player in estrogen (or hormone)-dependent breast cancer, and its action can be modified through many mechanisms (see a recent review by Manavathi et al. 2013) (33). Ross-Innes et al (34) provided an excellent example to show that changes in ER binding is associated with clinical outcome in breast cancer. There have been extensive studies of ER binding in estrogen-responsive cells/tissue through ChIP-on-chip and ER ChIP-seq analyses (30,35-38). From the ILLUMINA® ChIP-seq and Affymetrix microarray data presented herein, it is clear that the ER in LTEDaro cells behave differently from that in the MCF-7aro cells. The analysis of distance to transcription start site (TSS) shows that in the estrogen-responsive MCF-7aro cells, ER recruitment proximal to the TSS is dependent on E2, but in the resistant cells the ER recruitment to the same region can occur without E2. Comparison of the intensity and number of peaks reveals that in the MCF-7aro cells most of the ER binding is very weak without E2, and the ER binding is greatly enhanced when E2 is present.

On the other hand, in LTEDaro DMSO cells, a significant number of ER binding sites can be detected. ER binding data presented herein support previous proliferation studies (see, for example, (39). In the MCF-7aro cells, proliferation is entirely dependent on the E2-mediated activation of ER, and other growth factor pathways are not essential for the proliferation of these cells. LTEDaro cells are still dependent on the ER pathway for proliferation, as indicated by the fact that fulvestrant (ICI 182,780) is able to partially suppress the proliferation of LTEDaro (5). However, several signal transduction pathways have been activated leading to crosstalk with ER in this AI-resistant line (5).

HER2 is one of the important signaling proteins that play a role in the phosphorylation of ER, as in luminal B breast cancer (40). In accordance with the present invention, a MCF-7 cell line has been generated that over-expresses aromatase and HER2, i.e., HER2-aro. It has been shown that this line is resistant to both AIs and ICI (5). Comparison of ER binding sites between MCF-7aro DMSO and MCF-7aro E2 reveals that all the sites without E2 are very weak and in common with E2. Furthermore, addition of E2 to LTEDaro DMSO provides additional binding sites.

Through bioinformatics analysis, in combination with gene expression microarray data, SERPINA1 has been identified as one such ER target gene that clearly has E2-dependent ER binding in the hormone-responsive cells and E2-independent ER binding in the endocrine-resistant cells. Its expression in both types of cells is significantly suppressed by treatment with the ER degrader, fulvestrant. In accordance with the present invention, it is established that SERPINA1 is a direct ER target gene, as supported by ER ChIP-seq, ChIP PCR validation, microarray, and gene expression qPCR data.

Figure 3B:
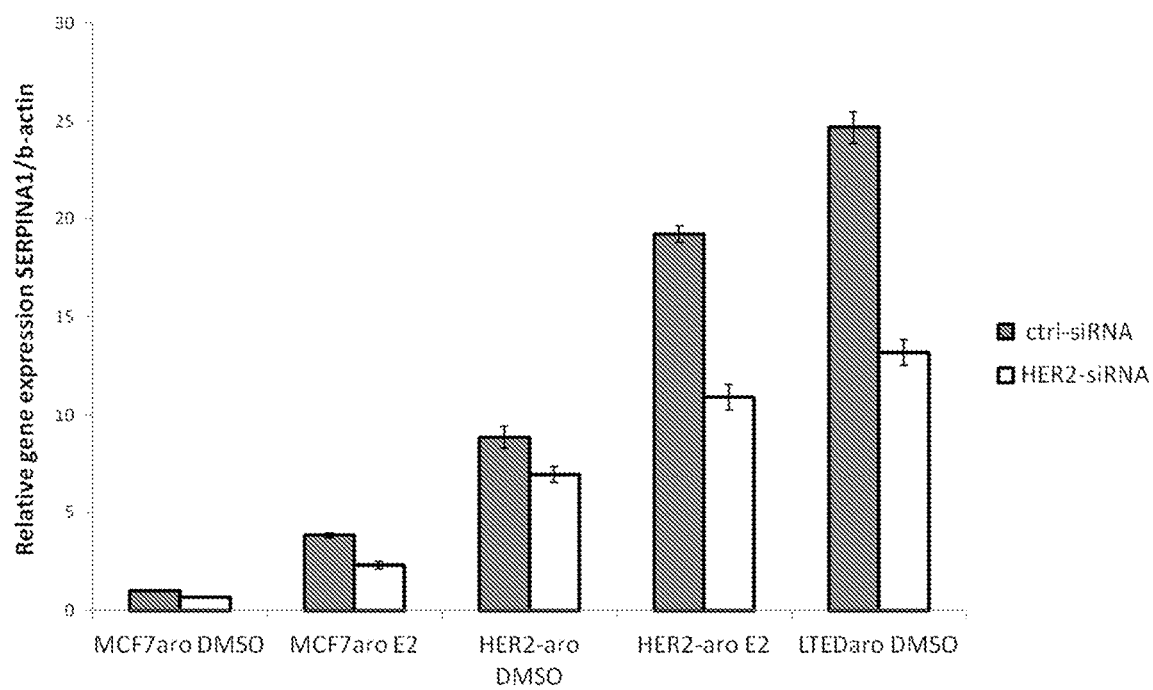

Based on the ChIP-seq data, the binding of ER to the promoter of the SERPINA1 gene is stronger in the LTEDaro DMSO cells compared to the MCF-7aro E2 cells. Considering the fact that SERPINA1 is highly expressed in LTE-Daro, its expression must be up-regulated by ER through cross-talk with growth factor-regulated pathways. From a search of GEO data, it has been found that SERPINA1 is also a HER2-regulated gene. This is supported by the fact that HER2-aro cells have much higher levels of SERPINA1 than MCF-7aro cells. The expression of SERPINA1 in these resistant cells is reduced upon the treatment of HER2 siRNA (see FIG. 3B). Based on the results presented herein, it is believed that in endocrine resistant cells (e.g., LTEDaro and HER2-aro), ER is activated through phosphorylation by signaling pathways activated by HER2 (5), and that SERPINA1 is a unique gene whose expression can be induced by phosphorylated ER (FIGS. 5A and 5B).

The present results provide an excellent example of how one can correlate ER binding data from bioinformatics experiments to patient outcome information. There are, however, some limitations to drawing such correlations. For example, multi-variate statistical analyses reveal that SERPINA1 expression has a significant association with patient survival in ER+ patients using the TCGA and Curtis cohorts, and with ER+/HER2+ patient survival in the TCGA and Bild patient cohorts. However, it was not possible to reach the same conclusion using four other patient cohorts (i.e., Chin, Pawitan, Desmedt, Sotiriou). This could be due to differences in the cohort size and/or composition of patient population of ER/PR/HER2 status in these cohorts.

The preceding observations point out the need for large cohorts with clinical outcome information for more meaningful prediction. Since the majority of breast cancer patients are ER+, the finding that SERPINA1 can predict survival in ER+ patients suggests that it may be a very useful prognostic marker; it is expected that many patients may benefit from this additional knowledge. Since the results described herein were not expected originally, the potential predictive value of SERPINA1 transcript expression levels in the ER+/HER2+ breast cancer is a particularly exciting development, especially since these patients have relatively poor prognosis.

Therefore, in certain embodiments of the present invention, in view of the clear correlation between SERPINA1 expression in ER+/HER2+ breast cancer, a subtype of breast cancer, the predictive value of SERPINA1 expression in ER+/HER2+ breast cancer has been fully established.

ER and HER2, two major regulatory pathways, cross-talk when they co-exist (41,42). Approximately 10 percent of breast cancer patients are ER+ and HER2+, and these patients have worse survival compared to ER+/HER2- and ER-/HER2+ patients (43). The ER+/HER2+ breast cancer is an important subtype of luminal B breast cancer (40). It has been also observed that a major number of recurring tumors from luminal A cancer are converted to luminal B HER2+ (40). Overexpression of HER2 in ER+ breast cancer is well recognized to affect the effectiveness of endocrine therapy, as observed preclinically (5) and clinically (44). Similarly, co-expression of ER is known to result in a poor trastuzumab response (45).

Previous studies have shown that in HER2+ breast tumors, the mRNA levels of HER2 is correlated with pathological complete response (pCR) rate only in ER+ patients but not in ER- patients (46). Extensive studies have been performed to demonstrate how ER-regulated pathways and HER2-regulator pathways can modulate each other (42). Preclinical experiments have found that LTEDaro, an AI-resistant model, is still partially responsive to ICI, but HER2-aro, a HER2-overexpressing line, fails to respond to either AI or ICI. These studies point out that in ER+ and HER2+ cancer(s), it is essential to suppress both regulatory pathways; as well as possibly suppressing additional mechanisms regulated by both of these pathways.

In ER+ breast cancers, the expression of SERPINA1 could be an indication of estrogen-mediated ER activation and its expression levels correlate to projected patient survival. An important finding described herein is the observation that SERPINA1 is an ER and HER2 regulated gene. While the level of SERPINA1 expression was found to be higher in endocrine resistant cells than responsive cells, survival analysis results suggest that the SERPINA1 gene can be a useful predictor of survival in ER and HER2 positive subgroup of breast cancer. A high expression of this gene is thought to be a strong indicator for the cooperative activation by both signaling pathways and to be a "good" response to both anti-ER and anti-HER2 therapies. Many ER-regulated genes, such as TFF1 (pS2), PGR and GREB1, are known to be induced in endocrine-resistant cancer. It is important to point out that the expression of these genes is not useful to predict the outcome of ER+/HER2- nor ER+/HER2+ cancer.

In early stage breast cancer, women with ER+ and HER2+ cancers are treated with adjuvant trastuzumab. Recent data suggest that a subset of these patients may not benefit from trastuzumab (47). Clinical data has shown that ER+/HER2+ patients generally have worse outcome than ER-/HER2+ or ER+/HER2- patients (17,18), and a predictive marker to predict a subgroup of patients with better outcome will be valuable.

Therefore, to investigate whether there are any differences in the treatments received by the patients with better survival compared to those with worse survival, the treatment information of ER+ and HER2+ patients in the TCGA cohort has been examined. The limited treatment information available for patients with high and low levels of SERPINA1 expression, which corresponds to better and worse survival groups, respectively, was compared. Most of the drugs used can be categorized under chemotherapy or endocrine therapy (see Table 1).

TABLE 1

|  | Drug name | # of patients | SERPINA1 high | SERPINA1 low |
|---|---|---|---|---|
| Chemo | 5-Fluorouracil | 4 | 3 | 1 |
| Chemo | ac | 1 | 1 | 0 |
| Chemo | Adriamycin | 5 | 1 | 3 |
| Chemo | adriamycin + cyclophosphamide | 1 | 0 | 1 |
| Endo | Arimidex | 8 | 4 | 4 |
| Endo | Aromasin | 2 | 2 | 0 |
| Chemo | Carboplatin | 3 | 0 | 3 |
| Chemo | Cyclophosphamide | 6 | 1 | 2 |
| Chemo | Cyclophosphane | 4 | 3 | 1 |
| Chemo | Cytoxan | 7 | 2 | 4 |
| Chemo | Docetaxel | 3 | 1 | 2 |
| Chemo | Doxorubicin | 9 | 4 | 2 |
| Chemo | doxorubicin + cyclophosphamid | 1 | 0 | 1 |
| Endo | Exemestane | 1 | 1 | 0 |
|  | Herceptin | 9 | 4 | 5 |
|  | Lapatinib | 2 | 0 | 2 |

TABLE 1-continued

| | Drug name | # of patients | SERPINA1 high | SERPINA1 low |
|---|---|---|---|---|
| Endo | Letrozole | 2 | 1 | 1 |
| Endo | Lupron | 1 | 0 | 0 |
| Chemo | Paclitaxel | 5 | 1 | 1 |
| Chemo | Paclitaxel (Protein-Bound) | 1 | 1 | 0 |
| Endo | Tamoxifen | 14 | 6 | 4 |
| Chemo | Taxol | 4 | 2 | 2 |
| Chemo | Taxotere | 5 | 2 | 3 |
| | Trastuzumab | 4 | 2 | 1 |
| Endo | Zoladex | 2 | 1 | 1 |
| | Zometa | 1 | 1 | 0 |
| | Total number of treatments: | 105 | 44 | 44 |
| | | Endo | 15 | 10 |
| | | Chemo | 22 | 26 |

Based on the comparison of the available treatment information of the patients with high and low levels of SERPINA1 expression, which corresponds to better and worse survival groups respectively, there are no major differences in the treatment strategies between good and bad responders, suggesting that SERPINA1 is an outcome predictor independent of treatment options. Chemotherapy and HER2-directed therapy is widely used as systemic treatment for patients with ER+ and HER2+ disease. Current molecular assays have not been able to distinguish a subset of HER2+ patients with better prognosis. Anti-HER2 therapy has been shown to improve endocrine therapy in ER+ and HER2+ positive cancer, as demonstrated in preclinical models (48, 49).

A recently completed trial has revealed that a combination of anti-HER2 therapy and endocrine therapy can be valuable to treat ER+ and HER2+ patients (50). Furthermore, from the EGF30008 and TAnDEM (TrAstuzumab in Dual HER2 ER-positive Metastatic breast cancer) trials, lapatinib+letrozole and trastuzumb+anastrozole were shown to improve time to progression versus AI monotherapy, respectively (51). A detailed analysis was reported by Delea et al. (51) that lapatinib+letrozole is not likely to be cost-effective than trastuzumab+anastrozole. Therefore, for those ER+ and HER2+ patients with high levels of SERPINA1 expression, a cost-effective treatment can be also considered.

BRIEF SUMMARY OF THE INVENTION

In one aspect, a method of determining an expression level of a SERPINA1 gene in a breast cancer patient is provided. The method includes (i) obtaining a biological sample from a breast cancer patient; and (ii) determining an expression level of a SERPINA1 gene in the biological sample.

In one aspect, a method of treating breast cancer in a subject in need thereof is provided. The method includes (i) determining whether a subject expresses an elevated level of a SERPINA1 gene relative to a standard control; and (ii) when an elevated expression level of the SERPINA1 gene is found relative to the standard control, administering to the subject an effective amount of an anti-ER therapy or an effective amount of an anti-HER2 therapy, thereby treating the subject.

In one aspect, a method of treating breast cancer in a subject in need thereof is provided. The method includes (i) determining whether a subject expresses an elevated level of a SERPINA1 gene relative to a standard control; and (ii) administering to the subject an effective amount of an anti-ER therapy or an effective amount of an anti-HER2 therapy, thereby treating the subject.

In one aspect, an in vitro complex is provided. The in vitro complex includes a labeled nucleic acid probe hybridized to a nucleic acid including a SERPINA1 gene sequence, wherein the nucleic acid is extracted from a breast cancer patient or is an amplification product of a nucleic acid extracted from a breast cancer patient.

In one aspect, an in vitro complex is provided. The in vitro complex includes a SERPINA1 polypeptide or fragment thereof bound to a SERPINA1 binding agent, wherein the SERPINA1 polypeptide or fragment thereof is extracted from a breast cancer patient.

In one aspect, a kit is provided. The kit includes (a) a labeled nucleic acid probe capable of hybridizing to a nucleic acid including a SERPINA1 gene sequence within a biological sample from a breast cancer patient, wherein the nucleic acid is extracted from the breast cancer patient or is an amplification product of a nucleic acid extracted from the breast cancer patient; and (b) a detecting reagent or a detecting apparatus capable of indicating hybridizing of the labeled nucleic acid probe to the nucleic acid.

In one aspect, a kit is provided. The kit includes (a) a SERPINA1 binding agent capable of binding to a SERPINA1 polypeptide or fragment thereof within a biological sample from a breast cancer patient; wherein the SERPINA1 polypeptide or fragment thereof is extracted from the breast cancer patient; and (b) a detecting reagent or a detecting apparatus capable of indicating binding of the SERPINA1 binding agent to the SERPINA1 polypeptide or fragment thereof bound.

Definitions

The terms "subject," "patient," "individual," and the like as used herein are not intended to be limiting and can be generally interchanged. That is, an individual described as a "patient" does not necessarily have a given disease, but may be merely seeking medical advice.

The term "subject" as used herein includes all members of the animal kingdom prone to suffering from the indicated disorder. In some aspects, the subject is a mammal, and in some aspects, the subject is a human.

A "control" sample or value refers to a sample that serves as a reference, usually a known reference, for comparison to a test sample. For example, a test sample can be taken from a patient suspected of having breast cancer and compared to samples from a known breast cancer patient, or a known normal (non-disease) individual. A control can also represent an average value gathered from a population of similar individuals, e.g., breast cancer patients or healthy individuals with a similar medical background, same age, weight, etc. A control value can also be obtained from the same individual, e.g., from an earlier-obtained sample, prior to disease, or prior to treatment. One of skill will recognize that controls can be designed for assessment of any number of parameters.

One of skill in the art will understand which controls are valuable in a given situation and be able to analyze data based on comparisons to control values. Controls are also valuable for determining the significance of data. For example, if values for a given parameter are widely variant in controls, variation in test samples will not be considered as significant.

As used herein, the terms "pharmaceutically" acceptable is used synonymously with physiologically acceptable and pharmacologically acceptable. A pharmaceutical composition will generally comprise agents for buffering and preservation in storage, and can include buffers and carriers for appropriate delivery, depending on the route of administration.

The terms "dose" and "dosage" are used interchangeably herein. A dose refers to the amount of active ingredient given to an individual at each administration. For the present invention, the dose will generally refer to the amount of breast cancer treatment. The dose will vary depending on a number of factors, including the range of normal doses for a given therapy, frequency of administration; size and tolerance of the individual; severity of the condition; risk of side effects; and the route of administration. One of skill will recognize that the dose can be modified depending on the above factors or based on therapeutic progress. The term "dosage form" refers to the particular format of the pharmaceutical, and depends on the route of administration. For example, a dosage form can be in a liquid form for nebulization, e.g., for inhalants, in a tablet or liquid, e.g., for oral delivery, or a saline solution, e.g., for injection.

As used herein, the terms "treat" and "prevent" are not intended to be absolute terms. Treatment can refer to any delay in onset, reduction in the frequency or severity of symptoms, amelioration of symptoms, improvement in patient comfort and/or respiratory function, etc. The effect of treatment can be compared to an individual or pool of individuals not receiving a given treatment, or to the same patient prior to, or after cessation of, treatment.

"Treating" or "treatment" as used herein (and as well-understood in the art) also broadly includes any approach for obtaining beneficial or desired results in a subject's condition, including clinical results. Beneficial or desired clinical results can include, but are not limited to, alleviation or amelioration of one or more symptoms or conditions, diminishment of the extent of a disease, stabilizing (i.e., not worsening) the state of disease, prevention of a disease's transmission or spread, delay or slowing of disease progression, amelioration or palliation of the disease state, diminishment of the reoccurrence of disease, and remission, whether partial or total and whether detectable or undetectable. In other words, "treatment" as used herein includes any cure, amelioration, or prevention of a disease. Treatment may prevent the disease from occurring; inhibit the disease's spread; relieve the disease's symptoms, fully or partially remove the disease's underlying cause, shorten a disease's duration, or do a combination of these things.

"Treating" and "treatment" as used herein include prophylactic treatment. Treatment methods include administering to a subject a therapeutically effective amount of an active agent. The administering step may consist of a single administration or may include a series of administrations. The length of the treatment period depends on a variety of factors, such as the severity of the condition, the age of the patient, the concentration of active agent, the activity of the compositions used in the treatment, or a combination thereof. It will also be appreciated that the effective dosage of an agent used for the treatment or prophylaxis may increase or decrease over the course of a particular treatment or prophylaxis regime. Changes in dosage may result and become apparent by standard diagnostic assays known in the art. In some instances, chronic administration may be required. For example, the compositions are administered to the subject in an amount and for a duration sufficient to treat the patient.

The term "therapeutically effective amount," as used herein, refers to that amount of the therapeutic agent (e.g., anti-ER therapy or anti-HER2 therapy) sufficient to ameliorate breast cancer, as described above. For example, for the given parameter, a therapeutically effective amount will show an increase or decrease of at least 5%, 10%, 15%, 20%, 25%, 40%, 50%, 60%, 75%, 80%, 90%, or at least 100%. Therapeutic efficacy can also be expressed as "-fold" increase or decrease. For example, a therapeutically effective amount can have at least a 1.2-fold, 1.5-fold, 2-fold, 5-fold, or more effect over a control.

The term "diagnosis" refers to a relative probability that a breast cancer is present in the subject. Similarly, the term "prognosis" refers to a relative probability that a certain future outcome may occur in the subject. For example, in the context of the present invention, prognosis can refer to the likelihood that an individual will develop a breast cancer, or the likely severity of the disease (e.g., severity of symptoms, rate of functional decline, survival, etc.). The terms are not intended to be absolute, as will be appreciated by any one of skill in the field of medical diagnostics.

"Nucleic acid" or "oligonucleotide" or "polynucleotide" or grammatical equivalents used herein means at least two nucleotides covalently linked together. Oligonucleotides are typically from about 5, 6, 7, 8, 9, 10, 12, 15, 25, 30, 40, 50 or more nucleotides in length, up to about 100 nucleotides in length. Nucleic acids and polynucleotides are a polymers of any length, including longer lengths, e.g., 200, 300, 500, 1000, 2000, 3000, 5000, 7000, 10,000, etc. A nucleic acid of the present invention will generally contain phosphodiester bonds, although in some cases, nucleic acid analogs are included that may have alternate backbones, comprising, e.g., phosphoramidate, phosphorothioate, phosphorodithioate, or O-methylphophoroamidite linkages (see Eckstein, Oligonucleotides and Analogues: A Practical Approach, Oxford University Press); and peptide nucleic acid backbones and linkages. Other analog nucleic acids include those with positive backbones; non-ionic backbones, and non-ribose backbones, including those described in U.S. Pat. Nos. 5,235,033 and 5,034,506, and Chapters 6 and 7, ASC Symposium Series 580, *Carbohydrate Modifications in Antisense Research*, Sanghui & Cook, eds. Nucleic acids containing one or more carbocyclic sugars are also included within one definition of nucleic acids. Modifications of the ribose-phosphate backbone may be done for a variety of reasons, e.g., to increase the stability and half-life of such molecules in physiological environments or as probes on a biochip. Mixtures of naturally occurring nucleic acids and analogs can be made; alternatively, mixtures of different nucleic acid analogs, and mixtures of naturally occurring nucleic acids and analogs may be made.

The terms "identical" or percent "identity," in the context of two or more nucleic acids (e.g., genomic sequences or subsequences or coding sequences) or polypeptide sequences, refer to two or more sequences or subsequences that are the same or have a specified percentage of amino acid residues or nucleotides that are the same (i.e., 50%, 55%, 60%, 65%, 70%, 75%, 80%, 85%, 90%, 91%, 92%, 93%, 94%, 95%, 96%, 97%, 98%, 99%, or more identity over a specified region), when compared and aligned for maximum correspondence over a comparison window, or designated region as measured using one of the following sequence comparison algorithms or by manual alignment and visual inspection. Such sequences are then said to be "substantially identical." This definition also refers to the compliment of a test sequence. Optionally, the identity exists over a region that is at least about 10 to about 100, about 20 to about 75, about 30 to about 50 amino acids or nucleotides in length.

An example of algorithms suitable for determining percent sequence identity and sequence similarity are the BLAST and BLAST 2.0 algorithms, which are described in Altschul et al., *Nuc. Acids Res.* 25:3389-3402 (1977) and Altschul et al., *J. Mol. Biol.* 215:403-410 (1990), respectively. As will be appreciated by one of skill in the art, the software for performing BLAST analyses is publicly available through the website of the National Center for Biotechnology Information (ncbi.nlm.nih.gov).

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers, those containing modified residues, and non-naturally occurring amino acid polymer.

The term "amino acid" refers to naturally occurring and synthetic amino acids, as well as amino acid analogs and amino acid mimetics that function similarly to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, e.g., an α carbon that is bound to a hydrogen, a carboxyl group, an amino group, and an R group, e.g., homoserine, norleucine, methionine sulfoxide, methionine methyl sulfonium. Such analogs may have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions similarly to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical or associated, e.g., naturally contiguous, sequences. Because of the degeneracy of the genetic code, a large number of functionally identical nucleic acids encode most proteins. For instance, the codons GCA, GCC, GCG and GCU all encode the amino acid alanine. Thus, at every position where an alanine is specified by a codon, the codon can be altered to another of the corresponding codons described without altering the encoded polypeptide. Such nucleic acid variations are "silent variations," which are one species of conservatively modified variations. Every nucleic acid sequence herein which encodes a polypeptide also describes silent variations of the nucleic acid. One of skill will recognize that in certain contexts each codon in a nucleic acid (except AUG, which is ordinarily the only codon for methionine, and TGG, which is ordinarily the only codon for tryptophan) can be modified to yield a functionally identical molecule. Accordingly, often silent variations of a nucleic acid which encodes a polypeptide is implicit in a described sequence with respect to the expression product, but not with respect to actual probe sequences.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention. Typically conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, *Proteins* (1984)).

A "label" or a "detectable moiety" is a composition detectable by spectroscopic, photochemical, biochemical, immunochemical, chemical, or other physical means. For example, useful labels include $^{32}P$, fluorescent dyes, electron-dense reagents, enzymes (e.g., as commonly used in an ELISA), biotin, digoxigenin, or haptens and proteins or other entities which can be made detectable, e.g., by incorporating a radiolabel into a peptide or antibody specifically reactive with a target peptide. Any method known in the art for conjugating an antibody to the label may be employed, e.g., using methods described in Hermanson, *Bioconjugate Techniques* 1996, Academic Press, Inc., San Diego.

A "labeled protein or polypeptide" or a "labeled nucleic acid probe" is a protein or nucleic acid that is bound, either covalently, through a linker or a chemical bond, or noncovalently, through ionic, van der Waals, electrostatic, or hydrogen bonds to a label such that the presence of the labeled protein or nucleic acid may be detected by detecting the presence of the label bound to the labeled protein or nucleic acid. Alternatively, methods using high affinity interactions may achieve the same results where one of a pair of binding partners binds to the other, e.g., biotin, streptavidin.

In some examples of the disclosed methods, when the expression level of a SERPINA1 gene is assessed, the level is compared with control expression level of the SERPINA1 gene. By control level is meant the expression level of SERPINA1 gene from a sample or subject lacking a disease (e.g. breast cancer), at a selected stage of a disease or disease state, or in the absence of a particular variable such as a therapeutic agent. Alternatively, the control level comprises a known amount of a SERPINA1 gene. Such a known amount correlates with an average level of subjects lacking a disease, at a selected stage of a disease or disease state, or in the absence of a particular variable such as a therapeutic agent. A control level also includes the expression level of a SERPINA1 gene from one or more selected samples or subjects as described herein. For example, a control level includes an assessment of the expression level of a SERPINA1 gene in a sample from a subject that does not have a disease (e.g. breast cancer), is at a selected stage of progression of a disease (e.g. breast cancer), or has not received treatment for a disease. Another exemplary control level includes an assessment of the expression level of a SERPINA1 gene in samples taken from multiple subjects that do not have a disease, are at a selected stage of progression of a disease, or have not received treatment for a disease.

When the control level includes the expression level of a SERPINA1 gene in a sample or subject in the absence of a therapeutic agent, the control sample or subject is optionally the same sample or subject to be tested before or after treatment with a therapeutic agent or is a selected sample or subject in the absence of the therapeutic agent. Alternatively, a control level is an average expression level calculated from a number of subjects without a particular disease. A control level also includes a known control level or value known in the art.

A SERPINA1 protein as provided herein includes any of the recombinant or naturally-occurring forms of the SERPIN PEPTIDASE INHIBITOR, CLADE A, MEMBER 1 (SERPINA1) also known as ALPHA-1-ANTITRYPSIN (AAT), PROTEASE INHIBITOR 1 (PI; PI1), ANTI-ELASTASE or ANTITRYPSIN, or variants or homologs thereof that maintain SERPINA1 protein activity (e.g. within at least 50%, 80%, 90%, 95%, 96%, 97%, 98%, 99% or 100% activity compared to SERPINA1 protein). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring SERPINA1 protein. In embodiments, the SERPINA1 protein is substantially identical to the protein identified by the UniProt reference number P01009 or a variant or homolog having substantial identity thereto. In embodiments, the SERPINA1 protein encoded by the sequence corresponding to NCBI reference number GI:383286745 or a variant or homolog having substantial identity thereto. In embodiments, the SERPINA1 protein is encoded by SEQ ID NO:9. The sequence of SEQ ID NO:9 is the sequence of NCBI reference number GI:383286745.

Methods

In one aspect, a method of determining an expression level of a SERPINA1 gene in a breast cancer patient is provided. The method includes (i) obtaining a biological sample from a breast cancer patient; and (ii) determining an expression level of a SERPINA1 gene in the biological sample. In embodiments, the determining includes (a) contacting a nucleic acid including a SERPINA1 gene sequence with a labeled nucleic acid probe, thereby forming a SERPINA1-labeled nucleic acid complex; and (b) detecting the SERPINA1-labeled nucleic acid complex.

In another aspect, a method of determining an expression level of a SERPINA1 gene in a breast cancer patient is provided. The method includes (i) obtaining a biological sample from a breast cancer patient; and (ii) determining an expression level of a SERPINA1 gene in the biological sample, wherein the determining includes (a) contacting a nucleic acid including a SERPINA1 gene sequence with a labeled nucleic acid probe, thereby forming a SERPINA1-labeled nucleic acid complex; and (b) detecting the SERPINA1-labeled nucleic acid complex.

In embodiments, the nucleic acid is an amplification product of a nucleic acid extracted from the breast cancer patient. In embodiments, the labeled nucleic acid probe is fluorescently labeled. In embodiments, the labeled nucleic acid probe has at least 10 nucleotides. In embodiments, the labeled nucleic acid probe includes at least 10 contiguous nucleotides of the sequence of SEQ ID NO:9 or the complement thereof. In embodiments, the labeled nucleic acid probe includes the sequence of SEQ ID NO:3 or SEQ ID NO:4. In embodiments, the biological sample is a blood-derived sample. In some further embodiments, the blood-derived sample is whole blood, serum or plasma. In embodiments, the biological sample is a tissue-derived sample. In further embodiments, the tissue-derived sample is a breast tissue-derived sample.

In embodiments, the breast cancer patient is an HER2+ breast cancer patient. A HER2+ breast cancer patient as provided herein is a breast cancer patient including HER2-expressing breast cancer cells.

A HER2 protein as provided herein includes any of the recombinant or naturally-occurring forms of the receptor tyrosine-protein kinase erbB-2 (HER2), also known as CD340 (cluster of differentiation 340), proto-oncogene Neu, Erbb2 (rodent), or ERBB2, or variants or homologs thereof that maintain HER2 kinase activity (e.g. within at least 50%, 80%, 90%, 95%, 96%, 97%, 98%, 99% or 100% activity compared to HER2 kinase). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring HER2 kinase. In embodiments, the HER2 kinase is substantially identical to the protein identified by the UniProt reference number P04626 or a variant or homolog having substantial identity thereto. In embodiments, the HER2 kinase is encoded by the sequence corresponding to NCBI reference number GI:584277101 or a variant or homolog having substantial identity thereto.

A ER protein as provided herein includes any of the recombinant or naturally-occurring forms of the estrogen receptor protein (ER), or variants or homologs thereof that maintain ER protein activity (e.g. within at least 50%, 80%, 90%, 95%, 96%, 97%, 98%, 99% or 100% activity compared to ER protein). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring ER protein. In embodiments, the ER protein is substantially identical to the protein identified by the UniProt reference number P03372 or a variant or homolog having substantial identity thereto. In embodiments, the ER protein is substantially identical to the protein identified by the UniProt reference number Q92731 or a variant or homolog having substantial identity thereto.

In embodiments, the breast cancer patient is an ER+/HER2+ breast cancer patient. A ER+/HER2+ breast cancer patient as provided herein is a breast cancer patient including breast cancer cells expressing ER and HER2.

In embodiments, the expression level of the SERPINA1 gene is elevated relative to a standard control. In embodiments, the method includes administering to the patient a therapeutically effective amount of an anti-ER therapy or a therapeutically effective amount of an anti-HER2 therapy. In embodiments, the method includes administering to the patient a therapeutically effective amount of a combination of an anti-ER therapy and an anti-HER2 therapy. An anti-ER therapy is commonly known in the art and refers an effective therapeutic amount of a substance capable of detectably decreasing the expression or activity of a ER gene or ER protein. The substance can decrease expression or activity 10%, 20%, 30%, 40%, 50%, 60%, 70%, 80%, 90% or more in comparison to a control in the absence of the substance. In certain instances, expression or activity is 1.5-fold, 2-fold, 3-fold, 4-fold, 5-fold, 10-fold or lower than the expression or activity in the absence of the substance. Likewise, an anti-HER2 therapy is commonly known in the art and refers an effective therapeutic amount of a substance capable of detectably decreasing the expression or activity of a HER2 gene or HER2 protein. The substance can decrease expression or activity 10%, 20%, 30%, 40%, 50%, 60%, 70%, 80%, 90% or more in comparison to a control in the absence of the substance. In certain instances, expression or activity is 1.5-fold, 2-fold, 3-fold, 4-fold, 5-fold, 10-fold or lower than the expression or activity in the absence of the substance.

In one aspect, a method of treating breast cancer in a subject in need thereof is provided. The method includes (i) determining whether a subject expresses an elevated level of a SERPINA1 gene relative to a standard control; and (ii) when an elevated expression level of the SERPINA1 gene is found relative to the standard control, administering to the subject an effective amount of an anti-ER therapy or an effective amount of an anti-HER2 therapy, thereby treating the subject. In embodiments, the method includes administering to the patient a therapeutically effective amount of a combination of an anti-ER therapy and an anti-HER2 therapy.

In one aspect, a method of treating breast cancer in a subject in need thereof is provided. The method includes (i) determining whether a subject expresses an elevated level of a SERPINA1 gene relative to a standard control; and (ii) administering to the subject an effective amount of an anti-ER therapy or an effective amount of an anti-HER2 therapy, thereby treating the subject. In embodiments, the administering occurs when an elevated expression level of the SERPINA1 gene is found relative to the standard control.

In Vitro Complexes

In one aspect, an in vitro complex is provided. The complex includes a labeled nucleic acid probe hybridized to a nucleic acid including a SERPINA1 gene sequence, wherein the nucleic acid is extracted from a breast cancer patient or is an amplification product of a nucleic acid extracted from a breast cancer patient. In embodiments, the labeled nucleic acid probe includes a detectable moiety as defined herein. Thus, in embodiments, the labeled nucleic acid probe is labeled with an isotope (e.g., $^{32}$P), a fluorescent dye, electron-dense reagents, enzymes (e.g., as commonly used in an ELISA), biotin, digoxigenin, or haptens and proteins or other entities which can be made detectable. In embodiments, the labeled nucleic acid probe is fluorescently labeled. In embodiments, the labeled nucleic acid probe has at least 10 nucleotides. In embodiments, the labeled nucleic acid probe includes at least 10 contiguous nucleotides of the sequence of SEQ ID NO:9 or the complement thereof. In embodiments, the labeled nucleic acid probe includes the sequence of SEQ ID NO:3 or SEQ ID NO:4. In embodiments, the more than one nucleic acid probe hybridized to the nucleic acid.

In embodiments, the nucleic acid is extracted from a blood-derived sample of the breast cancer patient. In embodiments, the nucleic acid is extracted from a tissue-derived sample of the breast cancer patient. In embodiments, the breast cancer patient is an HER2+ breast cancer patient. In embodiments, the breast cancer patient is an ER+/HER2+ breast cancer patient. In embodiments, the in vitro complex is in a detection device.

In another aspect, an in vitro complex is provided. The complex includes a SERPINA1 polypeptide or fragment thereof bound to a SERPINA1 binding agent, wherein the SERPINA1 polypeptide or fragment thereof is extracted from a breast cancer patient. In embodiments, the SERPINA1 polypeptide or fragment thereof is extracted from a blood-derived sample of the breast cancer patient. In embodiments, the SERPINA1 polypeptide or fragment thereof is extracted from a tissue-derived sample of the breast cancer patient. In embodiments, the SERPINA1 binding agent includes a detectable moiety. In embodiments, the SERPINA1 binding agent is an antibody.

In embodiments, the breast cancer patient is an HER2+ breast cancer patient. In embodiments, the breast cancer patient is an ER+/HER2+ breast cancer patient. In embodiments, the in vitro complex is attached to a solid support. In embodiments, the in vitro complex is in a detection device.

Kits

The invention provides kits for detection of SERPINA1 gene expression in a subject. The kit can be for personal use or provided to medical professionals. The kit can be a kit for diagnosing breast cancer, or for monitoring the progression of disease or the efficacy of treatment. The kit will generally include at least one vial, test tube, flask, bottle, syringe or other container means, into which the testing agent, can be suitably reacted or aliquoted. Kits can also include components for comparing results such as a suitable control sample, for example a positive and/or negative control. The kit can also include a collection device for collecting and/or holding the sample from the subject. The collection device can include a sterile swab or needle (for collecting blood), and/or a sterile tube (e.g., for holding the swab or a bodily fluid sample).

In one aspect, a kit is provided. The kit includes (a) a labeled nucleic acid probe capable of hybridizing to a nucleic acid including a SERPINA1 gene sequence within a biological sample from a breast cancer patient, wherein the nucleic acid is extracted from the breast cancer patient or is an amplification product of a nucleic acid extracted from the breast cancer patient; and (b) a detecting reagent or a detecting apparatus capable of indicating hybridizing of the labeled nucleic acid probe to the nucleic acid. In embodiments, the kit includes c) a sample collection device for collecting a sample from a breast cancer patient.

In one aspect, a kit is provided. The kit includes (a) a SERPINA1 binding agent capable of binding to a SERPINA1 polypeptide or fragment thereof within a biological sample from a breast cancer patient; wherein the SERPINA1 polypeptide or fragment thereof is extracted from the breast cancer patient; and (b) a detecting reagent or a detecting apparatus capable of indicating binding of the SERPINA1 binding agent to the SERPINA1 polypeptide or fragment thereof bound. In embodiments, the kit includes c) a sample collection device for collecting a sample from a breast cancer patient.

Further Aspects and Embodiments

Therefore, in accordance with one aspect of the present invention, there are provided methods of detecting SERPINA1 in a human breast cancer patient, said method comprising:
assaying a biological sample from the human breast cancer patient, and
detecting the presence of SERPINA1 therein.

As used herein, the terms "assay" or "assaying" refer to investigative (analytic) procedures in laboratory medicine, pharmacology, environmental biology, continuous delivery, molecular biology, and the like, for qualitatively assessing or quantitatively measuring the presence or amount (or the functional activity) of a target entity (the analyte), which can be a drug or biochemical substance or a cell in an organism or organic sample. The measured entity is generally called the analyte, or the measurand or the target of the assay.

Generally, assays involve biological material or phenomena which tend to be intrinsically more complex either in composition or in behavior or both. Thus reading of an assay may be quite noisy and may involve greater difficulties in interpretation than an accurate chemical titration. On the other hand, older generation qualitative assays, especially bioassays, may be much more gross and less quantitative (e.g., counting death or dysfunction of an organism or cells in a population, or some descriptive change in some body part of a group of animals).

As used herein, the terms "detect" or "detecting" refer to the act of discovering or ascertaining the existence, presence, or absence of a fact of interest.

In certain aspects and embodiments of the present invention, there are provided methods of detecting SERPINA1 in a human breast cancer patient, said method comprising:
obtaining a biological sample from the human breast cancer patient, and
assaying for the presence of SERPINA1 therein.

In certain aspects and embodiments of the present invention, there are provided methods of detecting SERPINA1 in a human breast cancer patient, said method comprising assaying a biological sample from the human breast cancer patient for the presence of SERPINA1 therein.

In certain aspects and embodiments of the present invention, there are provided methods of detecting SERPINA1 in a human breast cancer patient, said method comprising detecting the presence of SERPINA1 in a biological sample from the human breast cancer patient.

In certain aspects and embodiments of the present invention, the human breast cancer patient is an ER+ breast cancer patient or an HER2+ breast cancer patient.

In certain aspects and embodiments of the present invention, the human breast cancer patient is an ER+/HER2+ breast cancer patient.

In certain aspects and embodiments of the present invention, the level of SERPINA1 is determined. In a typical determination, patient samples with a minimum amount (e.g., 5 to 15 μg) of RNA can be selected. 1-2 μg of total RNA can be amplified and labeled for microarray hybridization. Arrays can be scanned (e.g., with Agilent Scanner) and probe information can be obtained (i.e., with Agilent's Feature Extraction Software). Quality control can be performed. Data can be normalized (e.g., Lowess normalization) and the ratio of the sample and reference can be log 2 transformed to create gene expression values. The term "log 2 transformed" refers in the usual and customary sense to taking the logarithm (base 2) of the argument to be log 2 transformed. The term "reference" in this context means a gene (other than SERPINA1) which gives rise to RNA in a cell, which RNA can be quantified by methods disclosed herein and methods known in the art. In embodiments, the reference is a constitutively active gene. In embodiments, the reference is β-actin. Absent express indication to the contrary, the term "gene expression value" refers to the log 2 transformed ratio of sample to reference results from the amplification step, as modified by subsequent quality control and normalization procedures. In studies disclosed herein, 18,624 genes were analyzed, which includes SERPINA1. For the TCGA ER+ patients (n=570) the median SERPINA1 gene expression was 4.03715, and for TCGA ER+/HER2+ patients (60 months, n=82) was 3.794205.

Accordingly, in embodiments the gene expression value of SERPINA1 is determined. In embodiments, the SERPINA1 gene expression value is compared to a threshold value. As used in this context, the term "threshold" in the context of SERPINA1 means a numeric criterion for a gene expression value above which a subject can be deemed to have a better prognosis for treatment, and below which the subject can be deemed to have a worse prognosis for treatment. In embodiments, the threshold can be in the range 0.1 to 10. In embodiments, the range is 1.0 to 10.0, 1.0 to 9.0, 1.0 to 8.0, 2.0 to 8.0, 2.0 to 7.0, 2.0 to 6.0, 2.2 to 5.8, 2.4 to 5.6, 2.6 to 5.4, 2.8 to 5.2 or 3.0 to 5.0. In embodiments, the threshold is 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, or 6.0. In embodiments, SERPINA1 is present at a level above 1, 2, 3, 4, 5, 6, 7, 8, 9, 10, 11, 12, 13, 14, 16, 16, 17, 18, 19, 20, 30, 40 or even 50, corresponding to a gene expression value (log 2) of about 0.00, 1.00, 1.58, 2.00, 2.32, 2.58, 2.81, 3.00, 3.17, 3.32, 3.46, 3.58, 3.70, 3.81, 3.91, 4.00, 4.09, 4.17, 4.24, 4.32, 4.91, 5.32 or even 5.64, respectively. In embodiments, SERPINA1 is present at a level above 16, corresponding to a gene expression value of 4.00.

In embodiments, the results of microarray analysis carried out using 1-2 μg total RNA isolated from a breast cancer specimen predicts a better treatment outcome if the gene expression value of SERPINA1 is above the threshold. In embodiments, the threshold is 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, or 6.0. In embodiments, the threshold is 3.0. In embodiments, the threshold is 3.5. In embodiments, the threshold is 4.0. In embodiments, the threshold is 4.5. In embodiments, the threshold is 5.0. In embodiments, the threshold is 5.5. In embodiments, the threshold is 6.0. In embodiments, the threshold is about 3.0. In embodiments, the threshold is about 3.5. In embodiments, the threshold is about 4.0. In embodiments, the threshold is about 4.5. In embodiments, the threshold is about 5.0. In embodiments, the threshold is about 5.5. In embodiments, the threshold is about 6.0. Absent express indication otherwise, the term "about" in the context of numeric value means the nominal value+/−10% thereof.

In certain aspects and embodiments of the present invention, there are provided methods of identifying a human breast cancer patient as an ER+ breast cancer patient or an HER2+ breast cancer patient, said method comprising:
obtaining a biological sample from the human breast cancer patient, and
assaying for the presence of SERPINA1 therein.

In certain aspects and embodiments of the present invention, there are provided methods of identifying a human breast cancer patient as an ER+/HER2+ breast cancer patient, said method comprising:
obtaining a biological sample from the human breast cancer patient, and
assaying for the presence of SERPINA1 therein.

In certain aspects and embodiments of the present invention, any of the methods described herein can further comprise administering an effective amount of a combination of anti-ER therapy and anti-HER2 therapy to those human breast cancer patients who express SERPINA1.

The term "subject" includes living organisms which express SERPINA1. The term "subject" includes animals (e.g., mammals, e.g., cats, dogs, horses, pigs, cows, goats, sheep, rodents, e.g., mice or rats, rabbits, squirrels, bears, primates (e.g., chimpanzees, monkeys, gorillas, and humans)), as well as chickens, ducks, peking ducks, geese, and transgenic species thereof. The term "subject," includes to a subject, e.g., a human, specifically chosen to receive anti-ER therapy and/or anti-HER2 therapy according to the present invention, or a composition containing same. Accordingly, in some embodiments, subjects include subjects who express SERPINA1. In some embodiments, a preferred subject is a human.

The terms "treatment" or "treating" of a subject includes the application or administration of anti-ER therapy and/or anti-HER2 therapy according to the present invention, or a composition containing same to a subject (or application or administration of anti-ER therapy and/or anti-HER2 therapy according to the present invention, or a composition containing same to a cell or tissue from a subject) with the purpose of stabilizing, curing, healing, alleviating, relieving, altering, remedying, less worsening, ameliorating, improving, or affecting the disease or condition, the symptom of the disease or condition, or the risk of (or susceptibility to) the disease or condition. The term "treating" refers to any indicia of success in the treatment or amelioration of an injury, pathology or condition, including any objective or subjective parameter such as abatement; remission; lessening of the rate of worsening; stabilization, diminishing of symptoms or making the injury, pathology or condition more tolerable to the subject; slowing in the rate of degeneration or decline; making the final point of degeneration less debilitating; or improving a subject's physical or mental well-being. In an embodiment, the term "treating" can include increasing a subject's life expectancy.

The term "therapeutically effective amount" refers to the amount of a compound which is effective to treat a subject, e.g., treat a subject expressing SERPINA1. The therapeutically effective amount may vary based on the particular disorder(s) the subject is suffering from, the age, weight, and lifestyle of a particular subject. In addition, the therapeutically effective amount may depend on the severity of the disease state, organ function, kidney function, or underlying disease (e.g., the subject may be suffering from an inflammatory disease, a malignant neoplasm, a chronic infection, or the like).

The dosage administered in the methods of the present disclosure may be selected such that desired pharmacokinetic parameters and/or biologically favorable parameters are obtained after administration of the compound of the disclosure to the subject.

The term "pharmaceutical formulation" includes pharmaceutical compositions as described herein. In a further embodiment, the pharmaceutical formulations are designed to have favorable biological properties which enhance the ability of the compounds of the disclosure to implement anti-ER therapy and/or anti-HER2 therapy.

The disclosure also pertains, at least in part, to a pharmaceutical composition comprising a therapeutically effective amount of anti-ER therapy and/or anti-HER2 therapy according to the present invention, or a composition containing same and a second agent. In a further embodiment, the therapeutically effective amount is effective to implement anti-ER therapy and/or anti-HER2 therapy.

In a further embodiment, the disclosure pertains to a packaged pharmaceutical composition. The packaged pharmaceutical composition includes a therapeutically effective amount of anti-ER therapy and/or anti-HER2 therapy according to the present invention, or a composition containing same, packaged in combination with a label or insert advising that the composition be administered in combination with a second agent. In a further embodiment, the therapeutically effective amount is effective to implement anti-ER therapy and/or anti-HER2 therapy.

In yet another further embodiment, the disclosure pertains to a packaged pharmaceutical composition, which includes a therapeutically effective amount of a second agent packaged in combination with a label or insert advising that the composition be administered in combination with anti-ER therapy and/or anti-HER2 therapy according to the present invention, or a composition containing same.

The term "label or insert" includes, but is not limited to all written, electronic, or spoken communication with the subject, or with any person substantially responsible for the care of the subject, regarding the administration of the compositions of the present disclosure. An insert may further include information regarding coadministration of the compositions of the present disclosure with other compounds or compositions, e.g., second agents. Additionally, an insert may include instructions regarding administration of the compositions of the present disclosure with (or without) food.

In yet another embodiment, the disclosure pertains to a packaged pharmaceutical composition, which includes a container holding a pharmaceutical composition comprising a therapeutically effective amount of anti-ER therapy and/or anti-HER2 therapy according to the present invention, or a composition containing same in combination with a label or insert advising that the composition be administered with (or without) food.

Anti-ER therapy and/or anti-HER2 therapy according to the present invention, or a composition containing same may be supplied in a solution with an appropriate solvent or in a solvent-free form (e.g., lyophilized). In another aspect of the disclosure, the agents and buffers necessary for carrying out the methods of the disclosure may be packaged as a kit. The kit may be commercially used according to the methods described herein and may include instructions for use in a method of the disclosure. Additional kit components may include acids, bases, buffering agents, inorganic salts, solvents, antioxidants, preservatives, or metal chelators. The additional kit components are present as pure compositions, or as aqueous or organic solutions that incorporate one or more additional kit components. Any or all of the kit components may optionally further comprise buffers.

Anti-ER therapy and/or anti-HER2 therapy according to the present invention, or a composition containing same may also be administered in a variety of ways, e.g., parenterally, intraperitoneally, intraspinally, intracerebrally, and the like. Dispersions can be prepared in glycerol, liquid polyethylene glycols, and mixtures thereof and in oils. Under ordinary conditions of storage and use, these preparations may contain a preservative to prevent the growth of microorganisms.

To administer anti-ER therapy and/or anti-HER2 therapy according to the present invention, or a composition containing same by other than parenteral administration, it may be necessary to coat the active agent with, or co-administer the active agent with, a material to prevent its inactivation. For example, anti-ER therapy and/or anti-HER2 therapy according to the present invention, or a composition containing same may be administered to a subject in an appropriate carrier, for example, liposomes, or a diluent. Pharmaceutically acceptable diluents include saline and aqueous buffer solutions. Liposomes include water-in-oil-in-water CGF emulsions as well as conventional liposomes (Strejan et al., *J. Neuroimmunol.* 7, 27 (1984)). It should be noted that the term "pharmaceutical composition" includes the "pharmaceutical formulations" described above.

Pharmaceutical compositions suitable for injectable use include sterile aqueous solutions (where water soluble) or dispersions and sterile powders for the extemporaneous preparation of sterile injectable solutions or dispersion. In all cases, the composition must be sterile and must be fluid to the extent that easy syringability exists. It must be stable under the conditions of manufacture and storage and must be preserved against the contaminating action of microorganisms such as bacteria and fungi.

Suitable pharmaceutically acceptable vehicles include, without limitation, any non-immunogenic pharmaceutical adjuvants suitable for oral, parenteral, nasal, mucosal, transdermal, intravascular (IV), intraarterial (IA), intramuscular (IM), and subcutaneous (SC) administration routes, such as phosphate buffer saline (PBS).

The vehicle can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, isotonic agents are included, for example, sugars, sodium chloride, or polyalcohols such as mannitol and sorbitol, in the composition. Prolonged absorption of the injectable compositions can be brought about by including in the composition an agent which delays absorption, for example, aluminum monostearate or gelatin.

Sterile injectable solutions can be prepared by incorporating the therapeutic agent in the required amount in an appropriate solvent with one or a combination of ingredients enumerated above, as required, followed by filtered sterilization. Generally, dispersions are prepared by incorporating the therapeutic agent into a sterile vehicle which contains a basic dispersion medium and the required other ingredients from those enumerated above. In the case of sterile powders for the preparation of sterile injectable solutions, the methods of preparation are vacuum drying and freeze-drying which yields a powder of the active ingredient (i.e., the compound of the disclosure) plus any additional desired ingredient from a previously sterile-filtered solution thereof.

Anti-ER therapy and/or anti-HER2 therapy according to the present invention, or compositions containing same can be orally administered, for example, with an inert diluent or an assimilable edible carrier. Anti-ER therapy and/or anti-HER2 therapy according to the present invention, or compositions containing same and other ingredients may also be enclosed in a hard or soft shell gelatin capsule, compressed into tablets, or incorporated directly into the subject's diet. For oral therapeutic administration, anti-ER therapy and/or anti-HER2 therapy according to the present invention, or a composition containing same may be incorporated with excipients and used in the form of ingestible tablets, buccal tablets, troches, capsules, elixirs, suspensions, syrups, wafers, and the like. The percentage of the anti-ER therapy and/or anti-HER2 therapy according to the present invention, or a composition containing same in the compositions and preparations may, of course, be varied. The amount of anti-ER therapy and/or anti-HER2 therapy according to the present invention, or a composition containing same in such therapeutically useful compositions is such that a suitable dosage will be obtained.

The present disclosure therefore includes pharmaceutical formulations comprising anti-ER therapy and/or anti-HER2 therapy according to the present invention, or a composition containing same, in pharmaceutically acceptable vehicles for aerosol, oral and parenteral administration. Also, the present disclosure includes such compounds, or salts thereof, which have been lyophilized and which may be reconstituted to form pharmaceutically acceptable formulations for administration, as by intravenous, intramuscular, or subcutaneous injection. Administration may also be intradermal or transdermal.

In accordance with the present disclosure, anti-ER therapy and/or anti-HER2 therapy according to the present invention, or a composition containing same may be administered orally or through inhalation as a solid, or may be administered intramuscularly or intravenously as a solution, suspension or emulsion. Alternatively, the agents or salts may also be administered by inhalation, intravenously or intramuscularly as a liposomal suspension.

Pharmaceutical compositions or formulations are also provided which are suitable for administration as an aerosol, by inhalation. These formulations comprise a solution or suspension of anti-ER therapy and/or anti-HER2 therapy according to the present invention, or a composition containing same, or a plurality of solid particles of the agent or salt. The desired formulation may be placed in a small chamber and nebulized. Nebulization may be accomplished by compressed air or by ultrasonic energy to form a plurality of liquid droplets or solid particles comprising the agents or salts. The liquid droplets or solid particles should have a particle size in the range of about 0.5 to about 5 microns. The solid particles can be obtained by processing the solid agent of an anti-ER therapy and/or anti-HER2 therapy according to the present invention, or a composition containing same, in any appropriate manner known in the art, such as by micronization. The size of the solid particles or droplets will be, for example, from about 1 to about 2 microns. In this respect, commercial nebulizers are available to achieve this purpose.

A pharmaceutical formulation suitable for administration as an aerosol may be in the form of a liquid, the formulation will comprise a water-soluble form of anti-ER therapy and/or anti-HER2 therapy according to the present invention, or a composition containing same, in a carrier which comprises water. A surfactant may be present which lowers the surface tension of the formulation sufficiently to result in the formation of droplets within the desired size range when subjected to nebulization.

Pharmaceutical compositions may also be coated by conventional methods, typically with pH or time-dependent coatings, such that the subject agent is released in the gastrointestinal tract in the vicinity of the desired topical application, or at various times to extend the desired action. Such dosage forms typically include, but are not limited to, one or more of cellulose acetate phthalate, polyvinylacetate phthalate, hydroxypropyl methyl cellulose phthalate, ethyl cellulose, waxes, shellac, and the like.

Other compositions useful for attaining systemic delivery of anti-ER therapy and/or anti-HER2 therapy according to the present invention, or a composition containing same include sublingual, buccal and nasal dosage forms. Such compositions typically comprise one or more of soluble filler substances such as sucrose, sorbitol and mannitol; and binders such as acacia, microcrystalline cellulose, carboxymethyl cellulose and hydroxypropyl methyl cellulose. Glidants, lubricants, sweeteners, colorants, antioxidants and flavoring agents disclosed above may also be included.

Anti-ER therapy and/or anti-HER2 therapy according to the present invention, or compositions containing same can also be administered topically to a subject, e.g., by the direct laying on or spreading of a composition containing same on the epidermal or epithelial tissue of the subject, or transdermally via a "patch". Such compositions include, for example, lotions, creams, solutions, gels and solids. These topical compositions may comprise an effective amount, usually at least about 0.1 wt %, or even from about 1 wt % to about 5 wt %, of an anti-ER therapy and/or anti-HER2 therapy according to the present invention, or a composition containing same. Suitable carriers for topical administration typically remain in place on the skin as a continuous film, and resist being removed by perspiration or immersion in water. Generally, the carrier is organic in nature and capable of having dispersed or dissolved therein the therapeutic agent. The carrier may include pharmaceutically acceptable emollients, emulsifiers, thickening agents, solvents, and the like.

Toxicity and therapeutic efficacy of such agents can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and can be expressed as the ratio LD50/ED50; usually a larger therapeutic index is more efficacious. While compounds that exhibit toxic side effects may be used, care should be taken to design a delivery system that targets such agents to the site of affected tissue in order to minimize potential damage to unaffected cells and, thereby, reduce side effects.

It is understood that appropriate doses depend upon a number of factors within the ken of the ordinarily skilled physician, veterinarian, or researcher. The dose(s) of anti-ER therapy and/or anti-HER2 therapy according to the present invention, or a composition containing same will vary, for example, depending upon the identity, size, and condition of the subject or sample being treated, further depending upon the route by which the composition is to be administered, if applicable, and the effect which the practitioner desires the anti-ER therapy and/or anti-HER2 therapy according to the present invention, or a composition containing same to have upon the subject. Exemplary doses include milligram or microgram amounts of anti-ER therapy and/or anti-HER2 therapy according to the present invention, or a composition containing same per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram).

It is furthermore understood that appropriate doses depend upon the potency. Such appropriate doses may be determined using assays known in the art. When an anti-ER therapy and/or anti-HER2 therapy according to the present invention, or a composition containing same is to be administered to an animal (e.g., a human), a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, and any drug combination.

Parenteral compositions may be formulated in dosage unit form for ease of administration and uniformity of dosage. Dosage unit form as used herein refers to physically discrete units suited as unitary dosages for the subjects to be treated; each unit containing a predetermined quantity of an anti-ER therapy and/or anti-HER2 therapy according to the present invention, or a composition containing same calculated to produce the desired therapeutic effect in association with the required pharmaceutical vehicle. The specifications for the dosage unit forms of the disclosure are dictated by and directly dependent on (a) the unique characteristics of the therapeutic agent and the particular therapeutic effect to be achieved, and (b) the limitations inherent in the art of compounding anti-ER therapy and/or anti-HER2 therapy according to the present invention, or compositions containing same for the prevention of infection with HIV.

In certain aspects and embodiments of the present invention, there are provided methods of identifying which therapeutic regimen is appropriate for a human breast cancer patient, said method comprising:
assaying a biological sample from the human breast cancer patient for the presence of SERPINA1 therein; and
administering to those human breast cancer patients which express SERPINA1 an effective amount of a combination of anti-ER therapy and anti-HER2 therapy.

The presence of SERPINA1 therein is indicative of an ER+ or ER+/HER2+ breast cancer patient. Thus, the physician is guided toward the use of treating agents and regimens which are consistent with such genetic profile.

In certain aspects and embodiments of the present invention, there are provided kits comprising:
(a) a SERPINA1 binding agent capable of binding to a SERPINA1 protein within a biological sample from a human subject with ER+ or ER+/HER2+ breast cancer; and
(b) a detecting reagent or a detecting apparatus capable of indicating binding of said SERPINA1 binding agent to said SERPINA1 protein.

In certain aspects and embodiments, the above-described kit is employed for the identification of a human subject as an ER+ or ER+/HER2+ breast cancer patient.

In certain aspects and embodiments of the present invention, there are provided kits comprising:
(a) a SERPINA1 binding agent capable of binding to a SERPINA1 protein within a biological sample from a human subject with ER+ or ER+/HER2+ breast cancer, said binding agent selected from the group consisting of:
(i) a SERPINA1 gene sequence;
(ii) a SERPINA1 RNA expressed from said SERPINA1 gene sequence or fragment thereof; and
(iii) a SERPINA1 protein expressed from said SERPINA1 gene sequence or fragment thereof, and
(b) a detecting reagent [e.g. a FRET probe] or a detecting apparatus capable of indicating binding of said SERPINA1 binding agent to said SERPINA1 protein.

In certain aspects and embodiments of the present invention, there are provided in vitro complexes comprising a SERPINA1 binding agent bound to a SERPINA1 protein, wherein said SERPINA1 protein is extracted from a human subject with ER+ or ER+/HER2+ breast cancer.

In some embodiments of the above-described in vitro complex, the SERPINA1 binding agent is bound to a solid support. Exemplary solid supports comprise a protein chip.

In certain aspects and embodiments of the present invention, there are provided in vitro complexes comprising a nucleic acid probe hybridized to a nucleic acid, said nucleic acid comprising a SERPINA1 gene sequence, wherein said nucleic acid is extracted from a human subject with ER+ or ER+/HER2+ breast cancer or is an amplification product of a nucleic acid extracted from a human subject with ER+ or ER+/HER2+ breast cancer.

In certain aspects and embodiments of the present invention, there are provided in vitro complexes comprising a thermally stable polymerase [e.g. a Taq polymerase] bound to a nucleic acid, said nucleic acid comprising a SERPINA1 gene sequence, wherein said nucleic acid is extracted from a human subject with ER+ or ER+/HER2+ breast cancer or is an amplification product of a nucleic acid extracted from a human subject with ER+ or ER+/HER2+ breast cancer.

In certain aspects and embodiments of the present invention, there are provided methods of treating breast cancer in a SERPINA1-expressing subject in need thereof, said method comprising administering to said subject an effective amount of a combination of anti-ER therapy and anti-HER2 therapy.

In certain aspects and embodiments of the present invention, there are provided methods of treating breast cancer in a SERPINA1-expressing subject in need thereof, said method comprising administering to said subject an effective amount of a nucleic acid or an antibody, wherein said nucleic acid is capable of hybridizing to a SERPINA1 gene or a SERPINA1 RNA, thereby decreasing levels of SERPINA1 protein in said subject, and wherein said antibody is capable of binding to a SERPINA1 protein thereby decreasing activity of said SERPINA1 protein, thereby treating breast cancer in the subject.

The following examples are provided to further illustrate aspects of the invention. These examples are non-limiting and should not be construed as limiting any aspect of the invention.

EXAMPLES

Example 1—Cell Lines

The MCF-7aro cell line was generated as a model line to study the action of AIs (3). The LTEDaro cell line was generated by a long-term estrogen deprivation of MCF-7aro and is used as a model of the late stage of endocrine resistance (4). HER2-aro is a MCF-7 line that over-expresses HER2 and aromatase (5) and is a model of de novo AI resistance as well as a model of luminal B, HER2-overexpressing subtype.

Example 2—ER ChIP-Seq Analysis

ER ChIP-seq analysis was performed to discover differences in ER binding between the endocrine-responsive (MCF-7aro) and endocrine-resistant (LTEDaro, Long-Term Estrogen Deprivation of MCF-7aro) cells. Comparing the ER binding sites discovered using deep sequencing and gene expression microarray data between LTEDaro DMSO and MCF-7aro E2, it was possible to identify direct ER target genes and correlate their expression to survival outcome using TCGA breast cancer patient cohort.

Thus, MCF-7aro and LTEDaro cells were cultured in hormone-free MEM for 5 days and serum-free MEM for 1 day. When the cell number reached about $1 \times 10^7$, both the LTEDaro and MCF-7aro cell lines were serum starved for 24 hours followed by treatment with 100 nM E2 or DMSO vehicle for 45 minutes, and cross-linked with 1% formaldehyde at room temperature for 10 minutes. Cells were enlarged in hypotonic buffer and nuclei were isolated by addition of NP-40 and centrifugation. The chromatin was sonicated to yield a majority of fragments with sizes between 100-300 base-pairs (bp). ERα antibodies (HC-20; sc-543) and IgG antibodies (sc-2027) from Santa Cruz Biotechnologies (Santa Cruz, Calif.) were used for the immunoprecipitation and control respectively. The enriched chromatin was purified with the QIAGEN® MINELUTE® PCR purification kit (Valencia, Calif.) and prepared for high-throughput sequencing.

The purified ChIP DNA samples were sequenced, using ILLUMINA® Solexa GENOME ANALYZER® II (San Diego, Calif.) at the DNA sequencing core facility (City of Hope, Duarte, Calif.), to generate short reads that are 36 to 45 bp in length. The short reads were mapped to human genome (Hg18) using the Bowtie (20) alignment tool. Peak-calling software, MACS v1.4.1 (21), was used to detect binding sites using the alignment results by setting a statistically significant cutoff (p-value=1.00e-5) comparing the ER versus IgG sample.

Most ER binding sites found in LTEDaro DMSO cells share the same location as those found in MCF-7aro treated with 17β-estradiol (E2). It was found that expression of the gene SERPINA1 has a significant predictive value for the overall survival (OS) of ER+ patients in the TCGA cohort; this finding was validated in the Curtis cohort. SERPINA1 also has a significant predictive value for the OS of ER+/HER2+ patients in the TCGA cohort, with validation in the Bild cohort. The expression of SERPINA1 in LTEDaro and MCF-7aro can be suppressed by ER degrader, fulvestrant (ICI 182,780), and HER2 siRNA.

The results presented herein indicate that HER2 constitutively activates ER, resulting in an E2-independent ER binding to the SERPINA1 gene and up regulating the expression of SERPINA1. Importantly, results of survival correlation analysis using large TCGA breast cancer cohort suggests that high expression of SERPINA1 could be predictive for a better clinical outcome of ER+ (4.03715 (max=11.0022, min=-0.927361)) and ER+/HER2+ (60 months=3.794205 (max=10.1786, min=0.992375)) breast cancer.

Example 3—Overlap Analysis of ER Binding Sites

The ER binding sites from MCF-7aro E2 and LTEDaro DMSO were selected by FDR≤0.5%, and the sites were labeled as "common" if there was at least 1 base-pair overlap, and the remainder of the sites were labeled as "unique". The ER binding sites associated with resistant cells were identified by comparing normalized binding site intensities of LTEDaro DMSO over MCF-7aro E2 with a change ratio≥0.9 as cutoff. A positive fold change of ≥0.9 indicates that LTEDaro DMSO binding sites have 90% or greater binding intensity compared to MCF-7aro E2. This group of "resistance-important" ER binding sites was annotated with genes within +/−20 kb, and were then integrated with the gene expression data from a previously described microarray study (1). The genes were filtered based on a cutoff of 1.2 fold change with FDR adjusted p<0.05; there were 350 genes that passed all filters.

Example 4—Kaplan-Meier Survival Analysis

To identify genes with potential survival predictive power, the 350 genes from the ER-binding site overlap analysis were ranked based on Cox scores, which represents the association of gene expression in patient cohorts with patient survival data. For a single gene survival correlation, patients were grouped as high expression and low expression subgroups based on the median expression of that gene. For a group of genes, patients were grouped as High-Risk and Low-Risk subgroups based on 2-means clustering of the selected significant genes for Kaplan-Meier survival analysis (22). Cox scores were calculated using R Bioconductor v3.0 and 2-means clustering analysis was performed in Partek Genomics Suite 6.6. Kaplan-Meier survival analysis was then used to determine the survival differences between the High-Risk and Low-Risk subgroups with p-values calculated by log-rank test in Partek Genomics Suite 6.6. The Cox score, which measures the correlation between the gene's expression level and patient survival, was calculated for each of the 350 genes. Based on the study by Bair and Tibshirani, a Cox score cutoff of 2.39 was used to select top genes with better survival correlation (22) resulting in a list of 35 genes. Using the TCGA breast cancer patient cohort as the training set (6), further analysis was performed, and a single gene discovered (and validated in the Curtis and Bild cohorts (23,24). In addition to the TCGA, Curtis and Bild cohorts, survival analysis has been performed on 4 other patient cohorts, namely Chin, Desmedt, Pawitan, and Sotiriou (25-28).

Figure 4C:
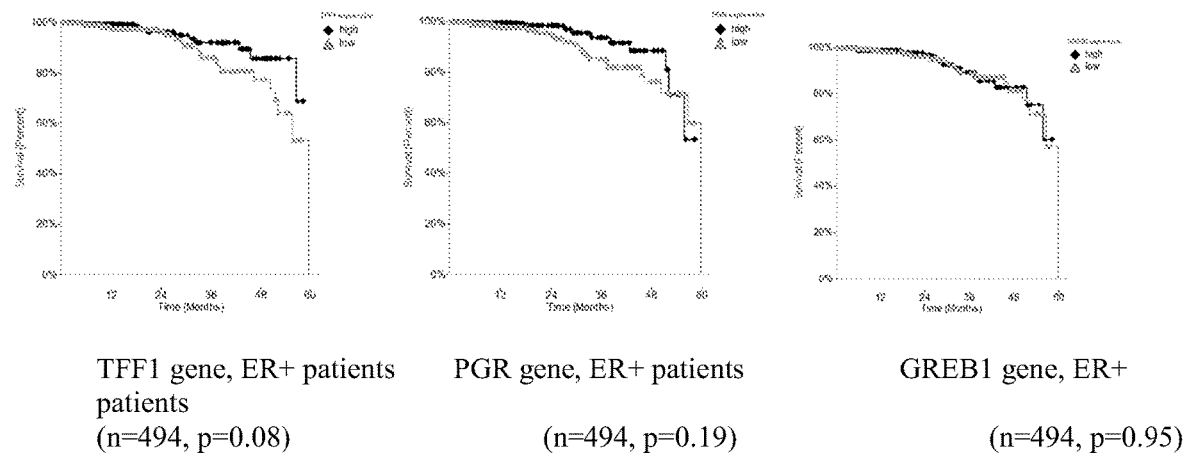
Figure 4D:
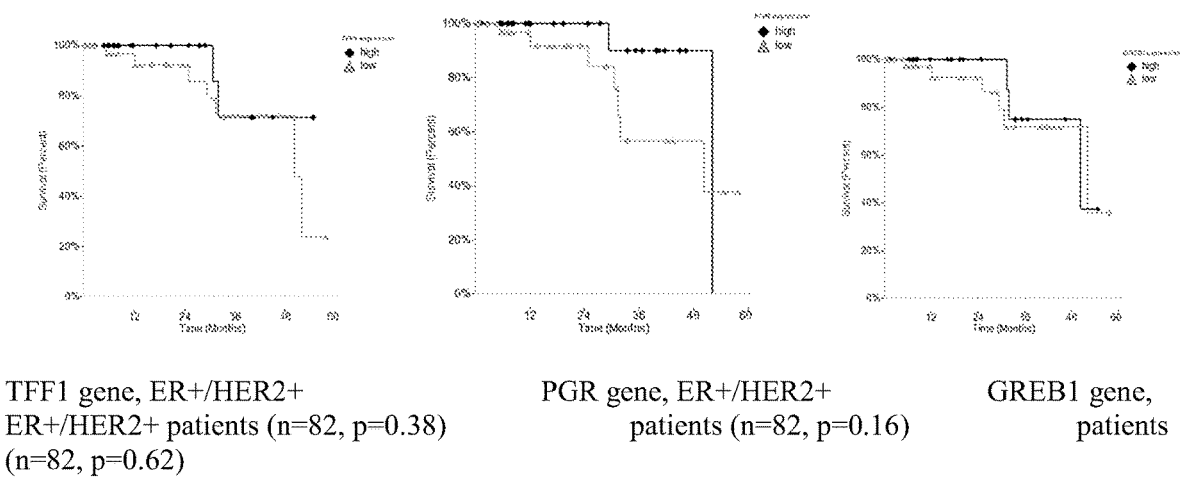

Additional Kaplan-Meier plots are presented in FIGS. 4C and 4D.

Example 5—Semi-Quantitative PCR Analysis of ER Binding

ChIP DNA was prepared as described above. Primers were designed to amplify a 166 bp region overlapping with the center of the peak as detected by ChIP-seq. The PCR was performed for 30 cycles using PROMEGA® GOTAQ® Green mastermix (Madison, Wash.) and analyzed by agarose gel electrophoresis.

Example 6—Quantitative PCR Analysis of SERPINA1 Expression

For gene expression quantification, LTEDaro and MCF-7aro cells were treated for 24 hours with E2, ICI 182780, and/or HER2 siRNA. RNA was extracted from cells with TRIZOL® reagent, and cDNA was synthesized with SUPERSCRIPT® III kit. Quantification of cDNA was performed using the BIO-RAD® iQ5 system. For the gene expression analysis, the delta Ct method was used, with β-actin as the normalizer. Exemplary primer sequences are provided in the following table:

| Target Name | Primer Sequence (5'-3') | SEQ ID NO: |
| --- | --- | --- |
| SERPINA1 F ChIP | GCCCGGCATGTCACCTGTTGTA | 1 |
| SERPINA1 R ChIP | CCTGCCAGTTATTGGTGCCAGGT | 2 |
| SERPINA1 F expression | CACCGTGAAGGTGCCTATGATG | 3 |
| SERPINA1 R expression | GGCATTGCCCAGGTATTTCATC | 4 |
| TFF1 F ChIP | TTCATGAGCTCCTTCCCTTC | 5 |
| TFF1 R ChIP | ATGGGAGTCTCCTCCAACCT | 6 |
| TFF1 F expression | AACAAGGTGATCTGCGCCCTG | 7 |
| TFF1 R expression | GGCGTGACACCAGGAAAACCA | 8 |

SERPINA1 gene expression primer sequences have been previously published (8).

Figure 1A:
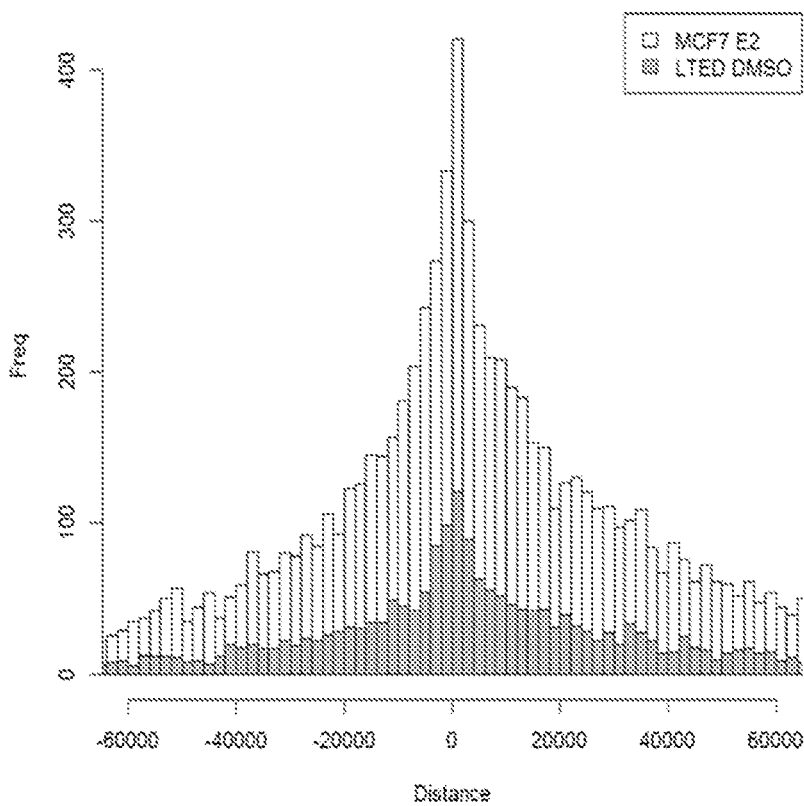
FIGS. 1A-1C collectively demonstrate that ER is able to bind chromatin independently of E2 in LTEDaro cells.
Figure 1B:
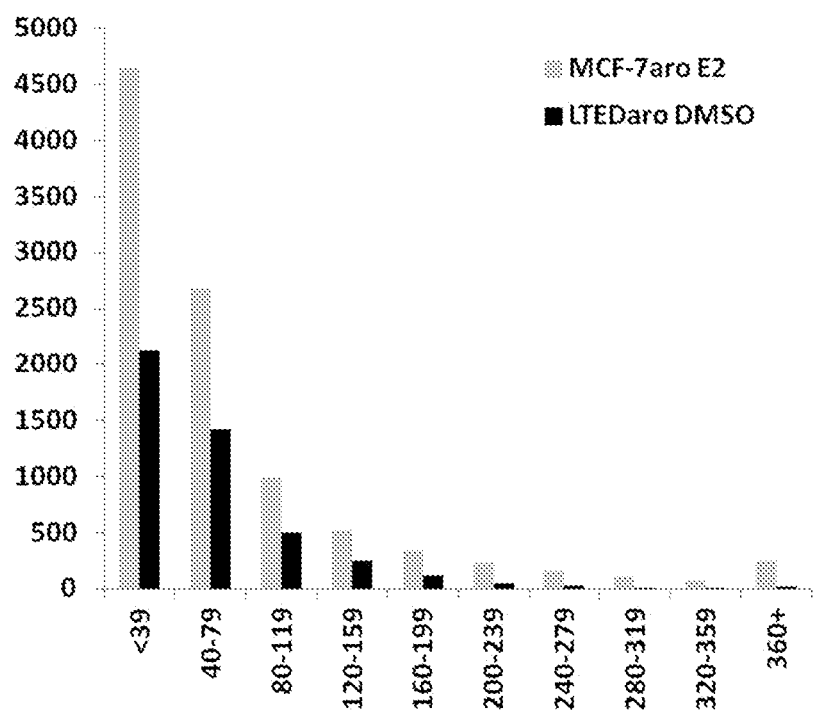

Example 7—Bioinformatics Analysis of ER ChIP-Seq and Microarray Expression Data The ER binding sites were then annotated with the genes, and the number of binding sites plotted against the distance to the closest transcription start sites (TSS). Comparison of the number of ER binding sites close to the TSS demonstrates that the distribution of the number of binding sites in the LTEDaro DMSO is comparable to that found in the MCF-7aro E2 (see FIG. 1A). This confirms that the ER binding in MCF-7aro is dependent on estrogens as expected, and most importantly, significant ER binding can occur without any hormones in LTEDaro cells. Analysis of the correlation between the number of binding sites and binding intensities also demonstrates that both LTEDaro DMSO and MCF-7aro E2 has a comparable normal distribution (see FIG. 1B).

Figure 1C:
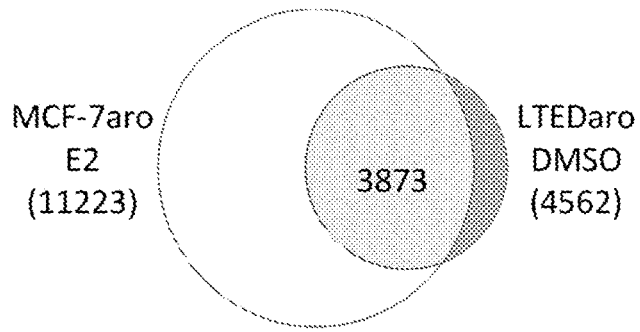

Based on the overlap analysis of ER binding sites described above, a comparison was performed between ER binding sites in hormone-independent LTEDaro DMSO and hormone-dependent MCF-7aro E2 cells, as shown in FIG. 1C. A majority of the binding sites were in the common group, but it should be emphasized that although the common sites shared the same location, the ER binding intensities were not always similar between LTEDaro DMSO and MCF-7aro E2.

Figure 2A:
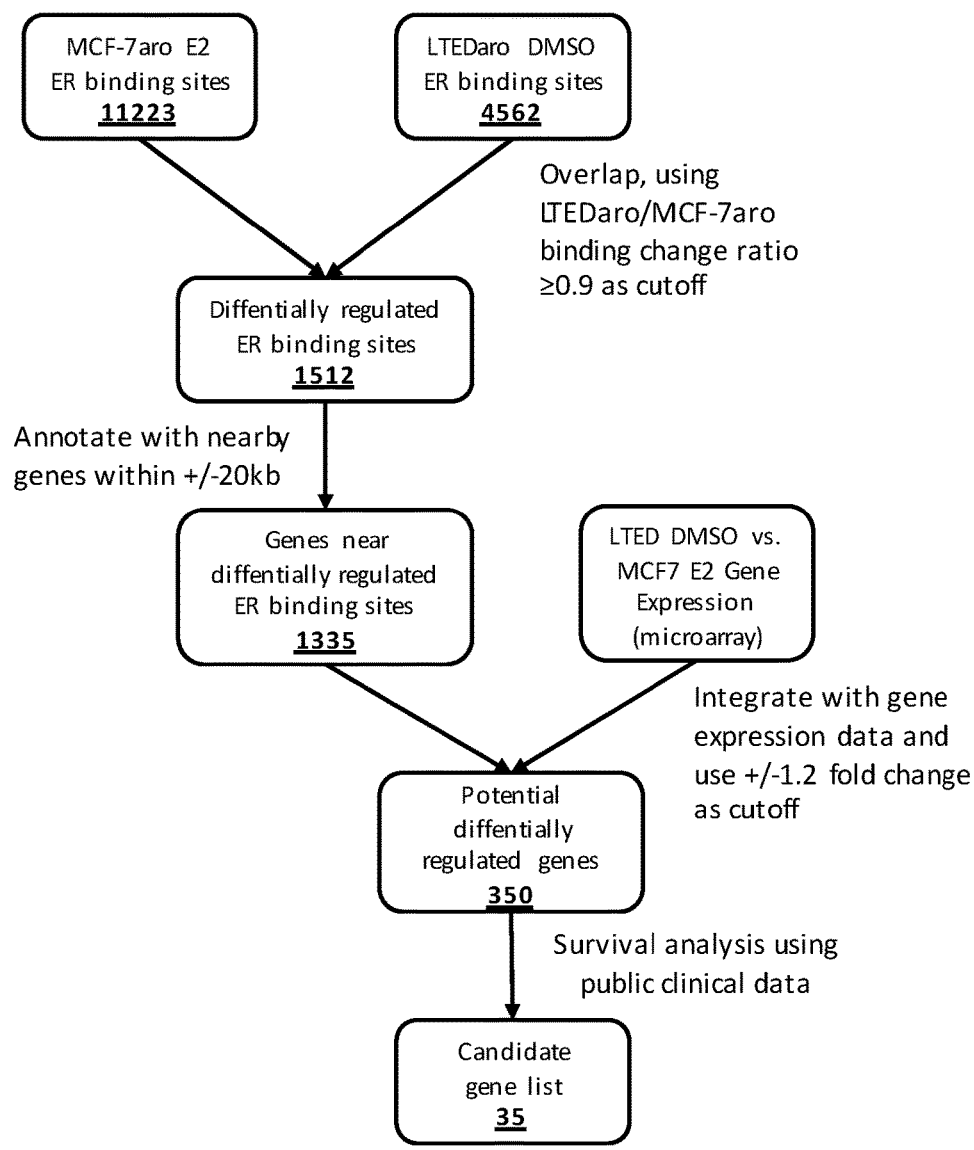
FIGS. 2A-2C collectively illustrate the identification of SERPINA1 as an ER target gene with a distinctive ER binding site in the promoter region.

FIG. 2A shows a comprehensive analysis workflow to determine the 350 differentially regulated genes, annotated for further validation using large patient cohorts with survival information.

Example 8—Survival Analysis in Breast Cancer Patient Cohorts

To determine the physiological significance of ER-binding genes in endocrine resistant cells, the resulting list of 350 genes was further analyzed for the ability to predict patient survival in TCGA breast cancer patient cohort with 570 ER+ only patients. 2-means clustering was adopted to cluster patients into high and low risk subgroups based on the 350 genes. As a whole, the group of 350 genes did not have a significant predictive value. As described above, using a Cox score cutoff of 2.39, the panel of 35 genes was further filtered for better survival correlation.

These 35 genes were then inspected individually in the IGV genome browser for ER binding site quality in order to narrow down the candidates for further qPCR validation and survival studies. As described above, ER binding sites that are of interest are those which are dependent on hormones in the MCF-7aro cells but have significant ER binding in the LTEDaro cells. During the visual inspection such factors as the overall intensity of ER binding, the distance of the binding from the TSS, the ratios of MCF-7aro E2 to MCF- 7aro DMSO binding, and ratios of LTEDaro DMSO to MCF-7aro E2 binding were taken into account. Based on these criteria, 3 genes were selected with negative Cox score and 8 genes were selected with positive Cox score from the panel of 35 genes.

Figure 2B:
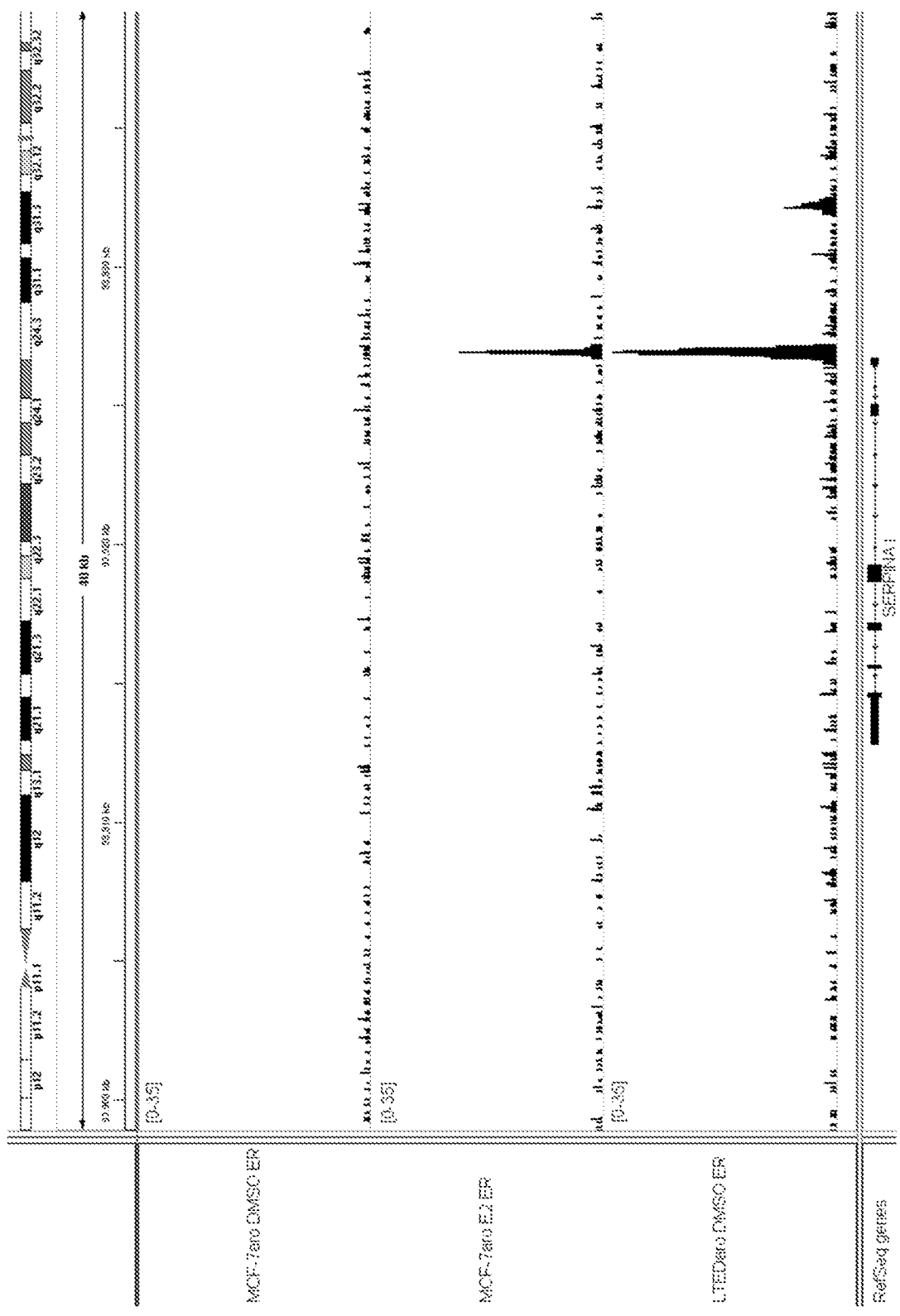

The 11 genes were then correlated with survival in ER+ and ER− patients using Kaplan Meier analysis. Based on p-values and biological relevance, it was decided to focus the analysis on one strong candidate with strong ER binding in LTEDaro DMSO, the SERPINA1 gene from the negative Cox score group. SERPINA1 was identified as a strong candidate since it has been reported to be an ER-regulated gene in breast cancer cells (20). As per the analyses described herein, SERPINA1 is observed to have a well-defined ER binding site with the distinctive property that ER binding in LTEDaro DMSO was found to be stronger than MCF-7aro E2 (FIG. 2B). According to the microarray data described herein, the expression level of this gene was about 3.4 fold higher in LTEDaro DMSO compared to MCF-7aro E2, and this difference is significantly higher according to the qPCR analysis summarized in FIG. 3A. As indicated by a negative Cox score, a higher expression of SERPINA1 was found to associate with a better overall survival in ER+ patients in the TCGA cohort (FIG. 4).

Example 9—the Promoter of SERPINA1 has an ER Binding Site

Figure 2C:
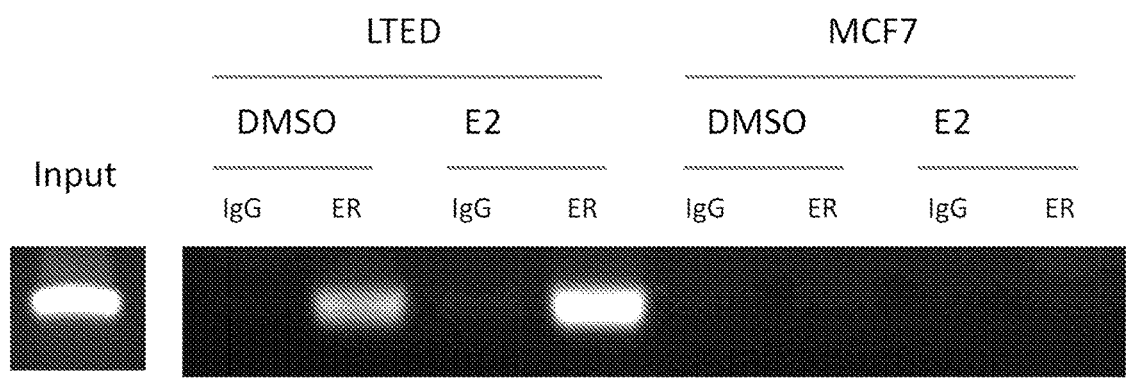
Figure 6:
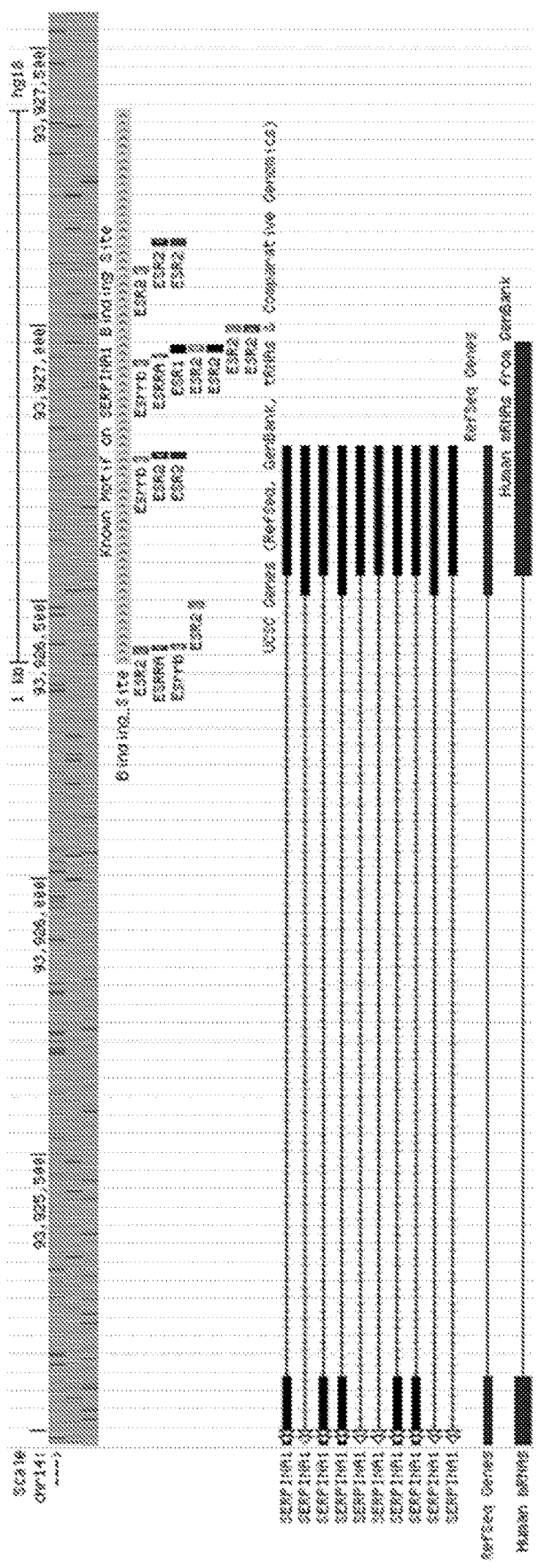
FIG. 6 demonstrates that the ER binding site at the SERPINA1 promoter contains an ERE. Known motif mapping of the ER binding site in the SERPINA1 promoter reveals the ERE motif in the center of the binding sites.

Although E2 was reported to up regulate the expression of SERPINA1 twenty years ago (7), the mechanism was unknown at that time. A direct ER-mediated regulation of its expression in MCF-7 cells was reported by Simpson et al. (29), and it was reported that E2 addition did not significantly enhance the ER binding to the ERE in the promoter of SERPINA1. The ER ChIP-seq analysis described herein confirms that the SERPINA1 gene has an ER binding site within the promoter region which overlaps with the TSS (see FIG. 2B), and the full ERE motif was found within this binding site by mapping known motifs (see FIG. 6), which agrees with the previous study by Simpson et al (20). In the MCF-7aro cells, the binding of ER to this site is dependent on estrogen, but in the LTEDaro DMSO cells, the ER binding has a higher intensity than MCF-7aro E2 even without estrogen. The ChIP PCR validation confirms the binding in LTEDaro DMSO (FIG. 2C).

Example 10—ER-Dependent and HER2-Dependent Regulation of SERPINA1 Expression in Endocrine-Responsive and -Resistant Cells In all cell lines examined herein, the SERPINA1 expression is up regulated with E2 treatment and suppressed by the ER degrader, fulvestrant (ICI 182,780) (see FIG. 3A). A search for SERPINA1 in the Gene Expression Omnibus (GEO) database provided support that SERPINA1 expression is stimulated by E2 in an ER-dependent manner (30, 31), and unexpectedly, by HER2 (32).

Since ER is known to be activated through ER-HER2 crosstalk in ER+/HER2+ cells/cancers, experiments were performed to determine whether the expression of SERPINA1 could be regulated by HER2. The expression level of SERPINA1 in two tested HER2-overexpressing cell lines, HER2-aro and LTEDaro cells, was found to be significantly higher than that in MCF-7aro cells, demonstrating that SERPINA1 is a HER2 regulated gene (see FIG. 3B). The HER2-dependent regulation of SERPINA1 expression was confirmed further by the down regulation of its expression by the treatment of siRNA targeting HER2 (see FIG. 3B).

Example 11—Significance of SERPINA1 Expression in ER+/HER2+ Breast Cancer

Based on the findings that SERPINA1 is regulated by both ER and HER2, Kaplan Meier survival analyses were then performed by dividing the patients into high and low expression groups based on the median of the single gene SERPINA1. It was found that this gene has a significant predictive value (p=0.00020) in 570 ER+ TCGA patient cohort (see FIG. 4A). In contrast, the same analysis performed on ER− patients was not statistically significant (see FIG. 4B), confirming that this is an ER-regulated gene. This finding was validated in the Curtis cohort with 986 ER+ patients (p=0.010) (see FIG. 4B).

To validate the findings from the TCGA cohort, survival analyses were carried out in four additional patient cohorts (24-25) (see Table 1). However, no correlation was observed between SERPINA1 levels and survival in four other cohorts of ER+ patients, namely Chin, Pawitan, Desmedt, Sotiriou. Since it has been confirmed that the expression of SERPINA1 can be also regulated by HER2, the HER2 status of patients in the six cohorts was checked, and it was found that only the TCGA, Curtis and Bild cohorts had a significant number of HER2-positive patients in ER+ subcohorts, whereas the other 4 cohorts had mostly HER2-negative patients or patients with unknown HER2 status in their ER+ subcohorts (Table 1). Such observations suggest that the HER2 status is related to the predictive value of SERPINA1 on patient survival.

To verify this hypothesis, further survival analysis was performed with subgroups of patients by separating the patients based on ER and HER2 status. In the TCGA cohort, the ER+ patients were subdivided based on HER2 status, and it was found that the SERPINA1 has a significant predictive value in the ER+/HER2+ group with 82 patients (p=0.045) but not the ER+/HER2− (FIG. 5A), ER−/HER2+, or ER−/HER2− patients.

For validation, the Bild cohort (24), with 61 ER+/HER2+ patients (24), and with a p-value is 0.075 (which is slightly above 0.05, perhaps due to the low number of ER+/HER2+ patients (Table 1), was used but the trend of separation can be observed visually (see FIG. 5B). The same analysis was performed on the Curtis ER+/HER2+ patients, and a visual separation of the two curves was also observed, but the curves intersect each other at the earlier timepoints, and the p-value is 0.14, so these results are not statistically significant. Similarly, no correlation was observed between SERPINA1 levels and survival in the other four cohorts of ER+ patients, namely Chin, Pawitan, Desmedt, Sotiriou.

Since it has been confirmed that the expression of SERPINA1 can be also regulated by HER2, the HER2 status of patients in the six cohorts was checked and it was found that only the TCGA and Bild cohorts had a significant number of HER2-positive patients in ER+ subcohorts, whereas the other 4 cohorts had mostly HER2-negative patients or patients with unknown HER2 status in their ER+ subcohorts, as summarized in the following table:

| Cohort | All patients DFS/OS | ER+ patients DFS/OS | ER+ patients Her2+/−/Unknown |
| --- | --- | --- | --- |
| TCGA | NA/779 | NA/570 | 88/318/164 |
| Bild | 170/158 | 114/110 | 61/40/13 |

| Cohort | All patients DFS/OS | ER+ patients DFS/OS | ER+ patients Her2+/−/Unknown |
|---|---|---|---|
| Chin | 117 (both) | 74 (both) | 4/45/25 |
| Desmedt | 198 (both) | 134 (both) | No Her2 status data |
| Pawitan | 159 (both) | 62 (both) | 0/62/0 |
| Sotiriou | 99 (both) | 65 (both) | No Her2 status data |

Such observations suggest that the HER2 status is related to the predictive value of SERPINA1 on patient survival. To verify this hypothesis, further survival analysis was performed with subgroups of patients by separating the patients based on ER and HER2 status. The results show that in the ER+/HER2+ patients in the TCGA cohort, SERPINA1 is able to separate patients into high and low risk groups (p-value=0.045), but no clear separation was observed in the ER+/HER2−, ER−/HER2+, or ER−/HER2− patients up to 60 months (see FIG. 5), but a clear separation in the ER+/HER2− (FIG. 5), ER−/HER2+, or ER−/HER2− patients was not observed. In the Bild cohort, it was possible to see a separation visually; however, the p-value is slightly above 0.05, perhaps due to the low number of ER+/HER2+ patients (see Table above).

To further establish the value and uniqueness of SERPINA1 as a predictive marker, the predictive ability of some well-known ER target genes TFF1 (pS2), PGR and GREB1 was investigated. The survival analyses were performed by grouping the patients in the TCGA cohort based on ER status only, and both ER and HER2 status. In ER+ and ER+/HER2+ patients, the 3 genes were not able to separate the patients into high and low risk groups. This further supports the unique ability of SERPINA1 to predict patient survival, because SERPINA1 is regulated by both ER and HER2.

Although the invention is illustrated and described herein with reference to specific embodiments, the invention is not intended to be limited to the details shown. Rather, various modifications may be made in the details within the scope and range of equivalents of the claims without departing from the invention.

REFERENCES

[1]. Masri S, Phung S, Wang X, Wu X, Yuan Y C, Wagman L, et al. Genome-wide analysis of aromatase inhibitor-resistant, tamoxifen-resistant, and long-term estrogen-deprived cells reveals a role for estrogen receptor. Cancer Res. 2008; 68:4910-8.

[2]. Clarke R, Leonessa F, Welch J N, Skaar T C. Cellular and molecular pharmacology of antiestrogen action and resistance. Pharmacological reviews. 2001; 53:25-71.

[3]. Zhou D J, Pompon D, Chen S A. Stable expression of human aromatase complementary DNA in mammalian cells: a useful system for aromatase inhibitor screening. Cancer Res. 1990; 50:6949-54.

[4]. Chen S, Masri S, Hong Y, Wang X, Phung S, Yuan Y C, et al. New experimental models for aromatase inhibitor resistance. J Steroid Biochem Mol Biol. 2007; 106:8-15.

[5]. Wong C, Wang X, Smith D, Reddy K, Chen S. AKT-aro and HER2-aro, models for de novo resistance to aromatase inhibitors; molecular characterization and inhibitor response studies. Breast Cancer Res Treat. 2012; 134:671-81.

[6]. Cancer Genome Atlas N. Comprehensive molecular portraits of human breast tumours. Nature. 2012; 490:61-70.

[7]. Finlay T H, Tamir S, Kadner S S, Cruz M R, Yavelow J, Levitz M. alpha 1-Antitrypsin- and anchorage-independent growth of MCF-7 breast cancer cells. Endocrinology. 1993; 133:996-1002.

[8]. Farshchian M, Kivisaari A, Ala-Aho R, Riihila P, Kallajoki M, Grenman R, et al. Serpin peptidase inhibitor Glade A member 1 (SerpinA1) is a novel biomarker for progression of cutaneous squamous cell carcinoma. The American journal of pathology. 2011; 179:1110-9.

[9]. Tan X F, Wu S S, Li S P, Chen Z, Chen F. Alpha-1 antitrypsin is a potential biomarker for hepatitis B. Virology journal. 2011; 8:274.

[10]. de Sa S V, Correa-Giannella M L, Machado M C, Krogh K, de Almeida M Q, Albergaria Pereira M A, et al. Serpin peptidase inhibitor clade A member 1 as a potential marker for malignancy in insulinomas. Clin Cancer Res. 2007; 13:5322-30.

[11]. Zhao W, Yang Z, Liu X, Tian Q, Lv Y, Liang Y, et al. Identification of alpha1-antitrypsin as a potential prognostic biomarker for advanced nonsmall cell lung cancer treated with epidermal growth factor receptor tyrosine kinase inhibitors by proteomic analysis. The Journal of international medical research. 2013; 41:573-83.

[12]. Vierlinger K, Mansfeld M H, Koperek O, Nohammer C, Kaserer K, Leisch F. Identification of SERPINA1 as single marker for papillary thyroid carcinoma through microarray meta analysis and quantification of its discriminatory power in independent validation. BMC medical genomics. 2011; 4:30.

[13]. Topic A, Ljujic M, Nikolic A, Petrovic-Stanojevic N, Dopudja-Pantic V, Mitic-Milikic M, et al. Alpha-1-antitrypsin phenotypes and neutrophil elastase gene promoter polymorphisms in lung cancer. Pathology oncology research: POR. 2011; 17:75-80.

[14]. Abbott K L, Aoki K, Lim J M, Porterfield M, Johnson R, O'Regan R M, et al. Targeted glycoproteomic identification of biomarkers for human breast carcinoma. Journal of proteome research. 2008; 7:1470-80.

[15]. Doustjalali S R, Yusof R, Yip C H, Looi L M, Pillay B, Hashim O H. Aberrant expression of acute-phase reactant proteins in sera and breast lesions of patients with malignant and benign breast tumors. Electrophoresis. 2004; 25:2392-401.

[16]. Lopez-Arias E, Aguilar-Lemarroy A, Felipe Jave-Suarez L, Morgan-Villela G, Mariscal-Ramirez I, Martinez-Velazquez M, et al. Alpha 1-antitrypsin: a novel tumor-associated antigen identified in patients with early-stage breast cancer. Electrophoresis. 2012; 33:2130-7.

[17]. Dawood S, Broglio K, Buzdar A U, Hortobagyi G N, Giordano S H. Prognosis of women with metastatic breast cancer by HER2 status and trastuzumab treatment: an institutional-based review. J Clin Oncol. 2010; 28:92-8.

[18]. Jerjees D A, Alabdullah M, Green A R, Alshareeda A, Macmillan R D, Ellis I O, et al. Prognostic and biological significance of proliferation and HER2 expression in the luminal class of breast cancer. Breast Cancer Res Treat. 2014.

[19]. Finn R S, Press M F, Dering J, O'Rourke L, Florance A, Ellis C, et al. Quantitative ER and PgR assessment as predictors of benefit from lapatinib in postmenopausal women with hormone receptor-positive, HER2-negative metastatic breast cancer. Clin Cancer Res. 2014; 20:736-43.

[20]. Langmead B, Trapnell C, Pop M, Salzberg S L. Ultrafast and memory-efficient alignment of short DNA sequences to the human genome. Genome Biol. 2009; 10:R25.

[21]. Zhang Y, Liu T, Meyer C A, Eeckhoute J, Johnson D S, Bernstein B E, et al. Model-based analysis of ChIP-Seq (MACS). Genome Biol. 2008; 9:R137.

[22]. Bair E, Tibshirani R. Semi-supervised methods to predict patient survival from gene expression data. PLoS biology. 2004; 2:E108.

[23]. Curtis C, Shah S P, Chin S F, Turashvili G, Rueda O M, Dunning M J, et al. The genomic and transcriptomic architecture of 2,000 breast tumours reveals novel subgroups. Nature. 2012; 486:346-52.

[24]. Bild A H, Yao G, Chang J T, Wang Q, Potti A, Chasse D, et al. Oncogenic pathway signatures in human cancers as a guide to targeted therapies. Nature. 2006; 439:353-7.

[25]. Chin K, DeVries S, Fridlyand J, Spellman P T, Roydasgupta R, Kuo W L, et al. Genomic and transcriptional aberrations linked to breast cancer pathophysiologies. Cancer cell. 2006; 10:529-41.

[26]. Desmedt C, Piette F, Loi S, Wang Y, Lallemand F, Haibe-Kains B, et al. Strong time dependence of the 76-gene prognostic signature for node-negative breast cancer patients in the TRANSBIG multicenter independent validation series. Clin Cancer Res. 2007; 13:3207-14.

[27]. Pawitan Y, Bjohle J, Amler L, Borg A L, Egyhazi S, Hall P, et al. Gene expression profiling spares early breast cancer patients from adjuvant therapy: derived and validated in two population-based cohorts. Breast cancer research: BCR. 2005; 7:R953-64.

[28]. Sotiriou C, Neo S Y, McShane L M, Korn E L, Long P M, Jazaeri A, et al. Breast cancer classification and prognosis based on gene expression profiles from a population-based study. Proc Natl Acad Sci USA. 2003; 100:10393-8.

[29]. Simpson N E, Gertz J, Imberg K, Myers R M, Garabedian M J. Research resource: enhanced genome-wide occupancy of estrogen receptor alpha by the cochaperone p23 in breast cancer cells. Mol Endocrinol. 2012; 26:194-202.

[30]. Lin C Y, Vega V B, Thomsen J S, Zhang T, Kong S L, Xie M, et al. Whole-genome cartography of estrogen receptor alpha binding sites. PLoS genetics. 2007; 3:e87.

[31]. Moggs J G, Murphy T C, Lim F L, Moore D J, Stuckey R, Antrobus K, et al. Anti-proliferative effect of estrogen in breast cancer cells that re-express ERalpha is mediated by aberrant regulation of cell cycle genes. J Mol Endocrinol. 2005; 34:535-51.

[32]. Creighton C J, Hilger A M, Murthy S, Rae J M, Chinnaiyan A M, El-Ashry D. Activation of mitogen-activated protein kinase in estrogen receptor alpha-positive breast cancer cells in vitro induces an in vivo molecular phenotype of estrogen receptor alpha-negative human breast tumors. Cancer Res. 2006; 66:3903-11.

[33]. Manavathi B, Dey O, Gajulapalli V N, Bhatia R S, Bugide S, Kumar R. Derailed estrogen signaling and breast cancer: an authentic couple. Endocrine reviews. 2013; 34:1-32.

[34]. Ross-Innes C S, Stark R, Teschendorff A E, Holmes K A, Ali H R, Dunning M J, et al. Differential oestrogen receptor binding is associated with clinical outcome in breast cancer. Nature. 2012; 481:389-93.

[35]. Carroll J S, Meyer C A, Song J, Li W, Geistlinger T R, Eeckhoute J, et al. Genome-wide analysis of estrogen receptor binding sites. Nat Genet. 2006; 38:1289-97.

[36]. Kininis M, Chen B S, Diehl A G, Isaacs G D, Zhang T, Siepel A C, et al. Genomic analyses of transcription factor binding, histone acetylation, and gene expression reveal mechanistically distinct classes of estrogen-regulated promoters. Mol Cell Biol. 2007; 27:5090-104.

[37]. Kwon Y S, Garcia-Bassets I, Hutt K R, Cheng C S, Jin M, Liu D, et al. Sensitive ChIP-DSL technology reveals an extensive estrogen receptor alpha-binding program on human gene promoters. Proc Natl Acad Sci USA. 2007; 104:4852-7.

[38]. Liu Y, Gao H, Marstrand T T, Strom A, Valen E, Sandelin A, et al. The genome landscape of ERalpha- and ERbeta-binding DNA regions. Proc Natl Acad Sci USA. 2008; 105:2604-9.

[39]. Wong C, Chen S. The development, application and limitations of breast cancer cell lines to study tamoxifen and aromatase inhibitor resistance. J Steroid Biochem Mol Biol. 2012; 131:83-92.

[40]. Falck A K, Bendahl P O, Chebil G, Olsson H, Ferno M, Ryden L. Biomarker expression and St Gallen molecular subtype classification in primary tumours, synchronous lymph node metastases and asynchronous relapses in primary breast cancer patients with 10 years' follow-up. Breast Cancer Res Treat. 2013; 140:93-104.

[41]. Takada M, Higuchi T, Tozuka K, Takei H, Haruta M, Watanabe J, et al. Alterations of the genes involved in the PI3K and estrogen-receptor pathways influence outcome in human epidermal growth factor receptor 2-positive and hormone receptor-positive breast cancer patients treated with trastuzumab-containing neoadjuvant chemotherapy. BMC Cancer. 2013; 13:241.

[42]. Giuliano M, Trivedi M V, Schiff R. Bidirectional Crosstalk between the Estrogen Receptor and Human Epidermal Growth Factor Receptor 2 Signaling Pathways in Breast Cancer: Molecular Basis and Clinical Implications. Breast Care (Basel). 2013; 8:256-62.

[43]. Howlader N, Altekruse S F, Li C I, Chen V W, Clarke C A, Ries L A, et al. U S Incidence of Breast Cancer Subtypes Defined by Joint Hormone Receptor and HER2 Status. J Natl Cancer Inst. 2014.

[44]. Collins L C, Schnitt S J. HER2 protein overexpression in estrogen receptor-positive ductal carcinoma in situ of the breast: frequency and implications for tamoxifen therapy. Modern pathology: an official journal of the United States and Canadian Academy of Pathology, Inc. 2005; 18:615-20.

[45]. Collins D C, Cocchiglia S, Tibbitts P, Solon G, Bane F T, McBryan J, et al. Growth factor receptor/steroid receptor cross talk in trastuzumab-treated breast cancer. Oncogene. 2014.

[46]. Denkert C, Huober J, Loibl S, Prinzler J, Kronenwett R, Darb-Esfahani S, et al. HER2 and ESR1 mRNA expression levels and response to neoadjuvant trastuzumab plus chemotherapy in patients with primary breast cancer. Breast cancer research: BCR. 2013; 15:R11.

[47]. Pogue-Geile K L, Kim C, Jeong J H, Tanaka N, Bandos H, Gavin P G, et al. Predicting degree of benefit from adjuvant trastuzumab in NSABP trial B-31. J Natl Cancer Inst. 2013; 105:1782-8.

[48]. Sabnis G, Schayowitz A, Goloubeva O, Macedo L, Brodie A. Trastuzumab reverses letrozole resistance and amplifies the sensitivity of breast cancer cells to estrogen. Cancer Res. 2009; 69:1416-28.

[49]. Chen B, Wang Y, Kane S E, Chen S. Improvement of sensitivity to tamoxifen in estrogen receptor-positive and Herceptin-resistant breast cancer cells. J Mol Endocrinol. 2008; 41:367-77.

[50]. Rimawi M F, Mayer I A, Forero A, Nanda R, Goetz M P, Rodriguez A A, et al. Multicenter phase II study of neoadjuvant lapatinib and trastuzumab with hormonal therapy and without chemotherapy in patients with human epidermal growth factor receptor 2-overexpressing breast cancer: TBCRC 006. J Clin Oncol. 2013; 31:1726-31.

[51]. Webber V L, Dixon J M. Role of endocrine therapy in ER+/HER2+ breast cancers. Breast Cancer Management. 2014; 3:103-11.

[52]. Delea T E, Hawkes C, Amonkar M M, Lykopoulos K, Johnston S R. Cost-Effectiveness of Lapatinib plus Letrozole in Post-Menopausal Women with Hormone Receptor- and HER2-Positive Metastatic Breast Cancer. Breast Care (Basel). 2013; 8:429-37.

EMBODIMENTS

Embodiment 1

A method of determining an expression level of a SERPINA1 gene in a breast cancer patient, said method comprising: (i) obtaining a biological sample from a breast cancer patient; and (ii) determining an expression level of a SERPINA1 gene in said biological sample.

Embodiment 2

The method of embodiment 1, wherein said determining comprises: (a) contacting a nucleic acid comprising a SERPINA1 gene sequence with a labeled nucleic acid probe, thereby forming a SERPINA1-labeled nucleic acid complex; and (b) detecting said SERPINA1-labeled nucleic acid complex.

Embodiment 3

The method of embodiment 2, wherein said nucleic acid is an amplification product of a nucleic acid extracted from said breast cancer patient.

Embodiment 4

The method of embodiment 2 or 3, wherein said labeled nucleic acid probe is fluorescently labeled.

Embodiment 5

The method of one of embodiments 2-4, wherein said labeled nucleic acid probe has at least 10 nucleotides.

Embodiment 6

The method of one of embodiments 2-5, wherein said labeled nucleic acid probe comprises at least 10 contiguous nucleotides of the sequence of SEQ ID NO:9 or the complement thereof.

Embodiment 7

The method of one of embodiments 2-6, wherein said labeled nucleic acid probe comprises the sequence of SEQ ID NO:3 or SEQ ID NO:4.

Embodiment 8

The method of one of embodiments 1-7, wherein said biological sample is a blood-derived sample.

Embodiment 9

The method of one of embodiments 1-7, wherein said biological sample is a tissue-derived sample.

Embodiment 10

The method of one of embodiments 1-9, wherein said breast cancer patient is an HER2+ breast cancer patient.

Embodiment 11

The method of one of embodiments 1-10, wherein said breast cancer patient is an ER+/HER2+ breast cancer patient.

Embodiment 12

The method of one of embodiments 1-11, wherein said expression level of said SERPINA1 gene is elevated relative to a standard control.

Embodiment 13

The method of one of embodiments 1-12, further comprising administering to said patient a therapeutically effective amount of an anti-ER therapy or a therapeutically effective amount of an anti-HER2 therapy.

Embodiment 14

The method of one of embodiments 1-13, further comprising administering to said patient a therapeutically effective amount of a combination of an anti-ER therapy and an anti-HER2 therapy.

Embodiment 15

A method of treating breast cancer in a subject in need thereof, said method comprising: (i) determining whether a subject expresses an elevated level of a SERPINA1 gene relative to a standard control; and (ii) when an elevated expression level of said SERPINA1 gene is found relative to said standard control, administering to said subject an effective amount of an anti-ER therapy or an effective amount of an anti-HER2 therapy, thereby treating said subject.

Embodiment 16

The method of embodiment 14, further comprising administering to said patient a therapeutically effective amount of a combination of an anti-ER therapy and an anti-HER2 therapy.

Embodiment 17

An in vitro complex comprising a labeled nucleic acid probe hybridized to a nucleic acid comprising a SERPINA1 gene sequence, wherein said nucleic acid is extracted from a breast cancer patient or is an amplification product of a nucleic acid extracted from a breast cancer patient.

Embodiment 18

The complex of embodiment 17, wherein said labeled nucleic acid probe is fluorescently labeled.

Embodiment 19

The complex of embodiment 17 or 18, wherein said labeled nucleic acid probe has at least 10 nucleotides.

Embodiment 20

The complex of one of embodiments 17-19, wherein said labeled nucleic acid probe comprises at least 10 contiguous nucleotides of the sequence of SEQ ID NO:9 or the complement thereof.

Embodiment 21

The complex of one of embodiments 17-20, wherein said labeled nucleic acid probe comprises the sequence of SEQ ID NO:3 or SEQ ID NO:4.

Embodiment 22

The complex of embodiment 17, comprising more than one nucleic acid probe hybridized to the nucleic acid.

Embodiment 23

The complex of one of embodiments 17-22, wherein said nucleic acid is extracted from a blood-derived sample of said breast cancer patient.

Embodiment 24

The complex of one of embodiments 17-22, wherein said nucleic acid is extracted from a tissue-derived sample of said breast cancer patient.

Embodiment 25

The complex of one of embodiments 17-24, wherein said breast cancer patient is an HER2+ breast cancer patient.

Embodiment 26

The complex of one of embodiments 17-25, wherein said breast cancer patient is an ER+/HER2+ breast cancer patient.

Embodiment 27

The complex of one of embodiments 17-26, wherein said in vitro complex is in a detection device.

Embodiment 28

An in vitro complex comprising a SERPINA1 polypeptide or fragment thereof bound to a SERPINA1 binding agent, wherein said SERPINA1 polypeptide or fragment thereof is extracted from a breast cancer patient.

Embodiment 29

The complex of embodiment 28, wherein said SERPINA1 polypeptide or fragment thereof is extracted from a blood-derived sample of said breast cancer patient.

Embodiment 30

The complex of embodiment 28, wherein said SERPINA1 polypeptide or fragment thereof is extracted from a tissue-derived sample of said breast cancer patient.

Embodiment 31

The complex of one of embodiments 28-30, wherein said SERPINA1 binding agent comprises a detectable moiety.

Embodiment 32

The complex of one of embodiments 28-31, wherein said SERPINA1 binding agent is an antibody.

Embodiment 33

The complex of one of embodiments 28-32, wherein said breast cancer patient is an HER2+ breast cancer patient.

Embodiment 34

The complex of one of embodiments 28-33, wherein said breast cancer patient is an ER+/HER2+ breast cancer patient.

Embodiment 35

The complex of one of embodiments 28-34, wherein said in vitro complex is attached to a solid support.

Embodiment 36

The complex of one of embodiments 28-35, wherein said in vitro complex is in a detection device.

Embodiment 37

A kit comprising: (a) a labeled nucleic acid probe capable of hybridizing to a nucleic acid comprising a SERPINA1 gene sequence within a biological sample from a breast cancer patient; wherein said nucleic acid is extracted from said breast cancer patient or is an amplification product of a nucleic acid extracted from said breast cancer patient; and (b) a detecting reagent or a detecting apparatus capable of indicating hybridizing of said labeled nucleic acid probe to said nucleic acid.

Embodiment 38

The kit of embodiment 37, further comprising: c) a sample collection device for collecting a sample from a breast cancer patient.

Embodiment 39

A kit comprising: (a) a SERPINA1 binding agent capable of binding to a SERPINA1 polypeptide or fragment thereof within a biological sample from a breast cancer patient; wherein said SERPINA1 polypeptide or fragment thereof is extracted from said breast cancer patient; and (b) a detecting reagent or a detecting apparatus capable of indicating binding of said SERPINA1 binding agent to said SERPINA1 polypeptide or fragment thereof.

Embodiment 40

The kit of embodiment 39, further comprising: c) a sample collection device for collecting a sample from a breast cancer patient.

Embodiment 41

A method of detecting SERPINA1 in a human breast cancer patient, said method comprising: assaying a biological sample from the human breast cancer patient, and detecting the presence of SERPINA1 therein.

Embodiment 42

The method of embodiment 41, wherein the human breast cancer patient is an ER+ breast cancer patient or an HER2+ breast cancer patient.

Embodiment 43

The method of embodiment 41, wherein the human breast cancer patient is an ER+/HER2+ breast cancer patient.

Embodiment 44

A method of identifying a human breast cancer patient as an ER+ breast cancer patient or an HER2+ breast cancer patient, said method comprising: obtaining a biological sample from the human breast cancer patient, and assaying for the presence of SERPINA1 therein.

Embodiment 45

A method of identifying a human breast cancer patient as an ER+ or ER+/HER2+ breast cancer patient, said method comprising: obtaining a biological sample from the human breast cancer patient, and assaying for the presence of SERPINA1 therein.

Embodiment 46

The method of one of embodiments 41-45, further comprising administering an effective amount of a combination of anti-ER therapy and anti-HER2 therapy to those human breast cancer patients who express SERPINA1.

Embodiment 47

A method of identifying which therapeutic regimen is appropriate for a human breast cancer patient, said method comprising: assaying a biological sample from the human breast cancer patient for the presence of SERPINA1 therein; and administering to those human breast cancer patients which express SERPINA1 an effective amount of a combination of anti-ER therapy and anti-HER2 therapy.

Embodiment 48

A kit comprising: (a) a SERPINA1 binding agent capable of binding to a SERPINA1 protein within a biological sample from a human subject with ER+ or ER+/HER2+ breast cancer; and (b) a detecting reagent or a detecting apparatus capable of indicating binding of said SERPINA1 binding agent to said SERPINA1 protein.

Embodiment 49

The kit of embodiment 48, wherein said human subject is an ER+/HER2+ breast cancer patient.

Embodiment 50

A kit comprising: (a) a SERPINA1 binding agent capable of binding to a SERPINA1 protein within a biological sample from a human subject with ER+ or ER+/HER2+ breast cancer, said binding agent selected from the group consisting of: (i) a SERPINA1 gene sequence; (ii) a SERPINA1 RNA expressed from said SERPINA1 gene sequence or fragment thereof; and (iii) a SERPINA1 protein expressed from said SERPINA1 gene sequence or fragment thereof, and (b) a detecting reagent [e.g. a FRET probe] or a detecting apparatus capable of indicating binding of said SERPINA1 binding agent to said SERPINA1 protein.

Embodiment 51

An in vitro complex comprising a SERPINA1 binding agent bound to a SERPINA1 protein, wherein said SERPINA1 protein is extracted from a human subject with ER+ or ER+/HER2+ breast cancer.

Embodiment 52

The in vitro complex according to embodiment 51 wherein the SERPINA1 binding agent is bound to a solid support.

Embodiment 53

The in vitro complex according to embodiment 52, wherein said solid support is a protein chip.

Embodiment 54

An in vitro complex comprising a nucleic acid probe hybridized to a nucleic acid, said nucleic acid comprising a SERPINA1 gene sequence, wherein said nucleic acid is extracted from a human subject with ER+ or ER+/HER2+ breast cancer or is an amplification product of a nucleic acid extracted from a human subject with ER+ or ER+/HER2+ breast cancer.

Embodiment 55

An in vitro complex comprising a thermally stable polymerase [e.g. a Taq polymerase] bound to a nucleic acid, said nucleic acid comprising a SERPINA1 gene sequence, wherein said nucleic acid is extracted from a human subject with ER+ or ER+/HER2+ breast cancer or is an amplification product of a nucleic acid extracted from a human subject with ER+ or ER+/HER2+ breast cancer.

Embodiment 56

A method of treating breast cancer in a SERPINA1-expressing subject in need thereof, said method comprising administering to said subject an effective amount of a combination of anti-ER therapy and anti-HER2 therapy.

Embodiment 57

A method of treating breast cancer in a SERPINA1-expressing subject in need thereof, said method comprising administering to said subject an effective amount of a nucleic acid or an antibody, wherein said nucleic acid is capable of hybridizing to a SERPINA1 gene or a SERPINA1 RNA, thereby decreasing levels of SERPINA1 protein in said subject, and wherein said antibody is capable of binding to a SERPINA1 protein thereby decreasing activity of said SERPINA1 protein, thereby treating breast cancer in the subject.

That which is claimed is:

1. A method of determining a prognosis for a breast cancer patient having an estrogen receptor (ER) status of positive and a HER2 status of positive (ER+/HER2+) based on an expression level of a single gene in a biological sample obtained from the breast cancer patient, wherein the single gene is SERPINA1, said method comprising:

(i) determining an expression level of the SERPINA1 gene in a biological sample obtained from the ER+/HER2+ breast cancer patient, by isolating total RNA from the sample and detecting SERPINA1 transcripts in the sample to determine a SERPINA1 gene expression level by a method comprising (a) contacting a nucleic acid sample obtained from the biological sample with a labeled nucleic acid probe comprising the sequence of SEQ ID NO:3 or SEQ ID NO:4, under conditions permitting the formation of a SERPINA1-labeled nucleic acid complex; and (b) detecting said SERPINA1-labeled nucleic acid complex to determine a SERPINA1 gene expression level;

(ii) comparing the SERPINA1 gene expression level to a threshold gene expression value to determine whether the SERPINA1 gene expression level is above or below the threshold value; and (iii) determining a prognosis for the ER+/HER2+ breast cancer patient based on the SERPINA1 gene expression level relative to the threshold gene expression value, wherein the prognosis for the ER+/HER2+ breast cancer patient is determined to be good where the SERPINA1 gene expression is above the threshold and the prognosis is determined to be poor where the SERPINA1 gene expression is below the threshold.

2. The method of claim 1, wherein said biological sample is a blood-derived or a tissue-derived sample.

3. The method of claim 1, further comprising administering to said patient a therapeutically effective amount of an anti-ER therapy or a therapeutically effective amount of an anti-HER2 therapy or a therapeutically effective amount of a combination of an anti-ER therapy and an anti-HER2 therapy.

4. A method of treating a breast cancer patient having an estrogen receptor (ER) status of positive and a HER2 status of positive (ER+/HER2+), the method comprising (i) determining an expression level of a single gene in a biological sample obtained from the patient, wherein the single gene is SERPINA1;

(ii) determining whether the expression level of the SERPINA1 gene is elevated relative to a standard control; and (iii) administering an effective amount of an anti-ER therapy or an effective amount of an anti-HER2 therapy to the ER+/HER2+ breast cancer patient having an elevated expression level of the SERPINA1 gene, thereby treating the subject.

* * * * *

SEQUENCE LISTING

```
<160> NUMBER OF SEQ ID NOS: 9

<210> SEQ ID NO 1
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 1
gcccggcatg tcacctgttg ta                                              22

<210> SEQ ID NO 2
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 2
cctgccagtt attggtgcca ggt                                             23

<210> SEQ ID NO 3
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 3
caccgtgaag gtgcctatga tg                                              22

<210> SEQ ID NO 4
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 4
ggcattgccc aggtatttca tc                                              22

<210> SEQ ID NO 5
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 5
ttcatgagct ccttcccttc                                                 20

<210> SEQ ID NO 6
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 6
```

```
atgggagtct cctccaacct                                                  20

<210> SEQ ID NO 7
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 7
aacaaggtga tctgcgccct g                                                21

<210> SEQ ID NO 8
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 8
ggcgtgacac caggaaaacc a                                                21

<210> SEQ ID NO 9
<211> LENGTH: 3207
<212> TYPE: DNA
<213> ORGANISM: Homo sapiens

<400> SEQUENCE: 9
ggcccacaga ggagcacagc tgtgtttggc tgcagggcca agagcgctgt caagaagacc       60
cacacgcccc cctccagcag ctgaattcct gcagctcagc agccgccgcc agagcaggac      120
gaaccgccaa tcgcaaggca cctctgagaa cttcaggatg cagatgtctc cagccctcac      180
ctgcctagtc ctgggcctgg cccttgtctt tggtgaaggg tctgctgtgc accatccccc      240
atcctacgtg gcccacctgg cctcagactt cggggtgagg gtgtttcagc aggtggcgca      300
ggcctccaag gaccgcaacg tggttttctc accctatggg gtggcctcgg tgttggccat      360
gctccagctg acaacaggag agaaaccca gcagcagatt caagcagcta tgggattcaa      420
gattgatgac aagggcatgg ccccgcctct ccggcatctg tacaaggagc tcatggggcc      480
atggaacaag gatgagatca gcaccacaga cgcgatcttc gtccagcggg atctgaagct      540
ggtccagggc ttcatgcccc acttcttcag gctgttccgg agcacggtca agcaagtgga      600
cttttcagag gtggagagag ccagattcat catcaatgac tgggtgaaga cacacacaaa      660
aggtatgatc agcaacttgc ttgggaaagg agccgtggac cagctgacac ggctggtgct      720
ggtgaatgcc ctctacttca acggccagtg gaagactccc ttccccgact ccagcaccca      780
ccgccgcctc ttccacaaat cagacggcag cactgtctct gtgcccatga tggctcagac      840
caacaagttc aactatactg agttcaccac gcccgatggc cattactacg acatcctgga      900 actgcctac cacggggaca ccctcagcat gttcattgct gccccttatg aaaaagaggt      960
gcctctctct gccctcacca acattctgag tgcccagctc atcagccact ggaaaggcaa     1020
catgaccagg ctgccccgcc tcctggttct gcccaagttc tccctggaga ctgaagtcga     1080
cctcaggaag cccctagaga acctgggaat gaccgacatg ttcagacagt ttcaggctga     1140
cttcacgagt ctttcagacc aagagcctct ccacgtcgcg caggcgctgc agaaagtgaa     1200
gatcgaggtg aacagagtg gcacggtggc ctcctcatcc acagctgtca tagtctcagc     1260
ccgcatggcc cccgaggaga tcatcatgga cagacccttc ctctttgtgg tccggcacaa     1320
```

```
cccccacagga acagtcctttt tcatgggcca agtgatggaa ccctgaccct ggggaaagac    1380
gccttcatct gggacaaaac tggagatgca tcgggaaaga agaaactccg aagaaaagaa    1440
ttttagtgtt aatgactctt tctgaaggaa gagaagacat ttgccttttg ttaaaagatg    1500
gtaaaccaga tctgtctcca agaccttggc ctctccttgg aggacctta ggtcaaactc    1560 cctagtctcc acctgagacc ctgggagaga agtttgaagc acaactccct taaggtctcc    1620
aaaccagacg gtgacgcctg cgggaccatc tggggcacct gcttccaccc gtctctctgc    1680
ccactcgggt ctgcagacct ggttcccact gaggcccttt gcaggatgga actacggggc    1740
ttacaggagc ttttgtgtgc ctggtagaaa ctatttctgt tccagtcaca ttgccatcac    1800
tcttgtactg cctgccaccg cggaggaggc tggtgacagg ccaaaggcca gtggaagaaa    1860
caccctttca tctcagagtc cactgtggca ctggccaccc ctccccagta cagggggtgct   1920 gcaggtggca gagtgaatgt cccccatcat gtgcccccaac tctcctggcc tggccatctc    1980
cctccccaga aacagtgtgc atgggttatt ttggagtgta ggtgacttgt ttactcattg    2040
aagcagattt ctgcttcctt ttatttttat aggaatagag gaagaaatgt cagatgcgtg    2100
cccagctctt caccccccaa tctcttggtg gggaggggtg tacctaaata tttatcatat    2160
ccttgcccct gagtgcttgt tagagagaaa gagaactact aaggaaaata atattattta    2220
aactcgctcc tagtgtttct ttgtggtctg tgtcaccgta tctcaggaag tccagccact    2280
tgactggcac acaccctcc ggacatccag cgtgacggag cccacactgc caccttgtgg    2340
ccgcctgaga ccctcgcgcc ccccgcgccc ctcttttttcc ccttgatgga aattgaccat    2400
acaatttcat cctccttcag gggatcaaaa ggacggagtg ggggggacaga gactcagatg    2460 aggacagagt ggtttccaat gtgttcaata gatttaggag cagaaatgca aggggctgca    2520
tgacctacca ggacagaact ttccccaatt acagggtgac tcacagccgc attggtgact    2580
cacttcaatg tgtcatttcc ggctgctgtg tgtgagcagt ggacacgtga gggggggtg    2640 ggtgagagag acaggcagct cggattcaac taccttagat aatatttctg aaaacctacc    2700
agccagaggg tagggcacaa agatggatgt aatgcacttt ggggaggccaa ggcgggagga    2760 ttgcttgagc ccaggagttc aagaccagcc tgggcaacat accaagaccc ccgtctcttt    2820
aaaaatatat atattttaaa tacttaaa tatatatttc taatatcttt aaatatat    2880 atatattta aagaccaatt tatgggagaa ttgcacacag atgtgaaatg aatgtaatct    2940
aatagaagcc taatcagccc accatgttct ccactgaaaa atcctctttc tttggggttt    3000
ttctttcttt cttttttgat tttgcactgg acggtgacgt cagccatgta caggatccac    3060
aggggtggtg tcaaatgcta ttgaaattgt gttgaattgt atgcttttc acttttgata    3120 aataaacatg taaaaatgtt tcaaaaaat aataaaataa ataaatacga agaatatgtc    3180
aggacagtca aaaaaaaaaa aaaaaaa                                         3207
```